(12) United States Patent
Vogiatzis

(10) Patent No.: US 10,172,914 B2
(45) Date of Patent: Jan. 8, 2019

(54) COMBINATION

(71) Applicant: Genesis Pharma SA, Athens (GR)

(72) Inventor: George Vogiatzis, Athens (GR)

(73) Assignee: GENESIS PHARMA SA, Athens (GR)

( * ) Notice: Subject to any disclaimer, the term of this patent is extended or adjusted under 35 U.S.C. 154(b) by 0 days.

(21) Appl. No.: 15/672,841

(22) Filed: Aug. 9, 2017

(65) Prior Publication Data

US 2017/0333519 A1 Nov. 23, 2017

Related U.S. Application Data

(63) Continuation of application No. PCT/IB2016/001582, filed on Nov. 4, 2016.

(30) Foreign Application Priority Data

Nov. 6, 2015 (GR) .............................. 20150100486

(51) Int. Cl.
| | |
|---|---|
| A61P 5/40 | (2006.01) |
| A61K 31/56 | (2006.01) |
| A61K 38/13 | (2006.01) |
| A61K 38/26 | (2006.01) |
| A61K 31/585 | (2006.01) |
| C07K 14/605 | (2006.01) |

(52) U.S. Cl.
CPC .............. *A61K 38/13* (2013.01); *A61K 31/56* (2013.01); *A61K 31/585* (2013.01); *A61K 38/26* (2013.01); *A61P 5/40* (2018.01); *C07K 14/605* (2013.01)

(58) Field of Classification Search
None
See application file for complete search history.

(56) References Cited

U.S. PATENT DOCUMENTS

2004/0214804 A1   10/2004   Gulve et al.

FOREIGN PATENT DOCUMENTS

| WO | 2004082599 A2 | 9/2004 |
| WO | 2013059323 A1 | 4/2013 |

OTHER PUBLICATIONS

Mayo Clinic Staff, "Myocardial Ischemia, Treatment and drugs," available online at http://www.mayoclinic.org/diseases-conditions/myocardial-ischemia/basics/treatment/con-20035096, 3 pages (2015).*
"Acute Myocardial Infarction," MedicineNet.com, available online at https://www.medicinenet.com/script/main/art.asp?articlekey=7489, 2 pages (2017) (Year: 2017).*
"Exenatide", DrugBank, Accession No. DB01276, 7 pages (accessed on Oct. 28, 2017) (Year: 2017).*
"Early Mineralocorticoid Receptor Antagonist Treatment to Reduce Myocardial Infarct Size," ClinicalTrials.gov, ClinicalTrials.gov Identifier NCT01882179, 9 pages (2013) (Year: 2013).*
Gupta, Indian J. Endocrinol. Metab. 17:413-421 (2013) (Year: 2013).*
Bai et al. (2015) "Revisiting cerebral postischemic reperfusion injury: new insights in understanding reperfusion failure, hemorrhage, and edema," International Journal of Stroke. 10(2):143-152.
Berge et al. (1977) "Pharmaceutical salts," Journal of pharmaceutical sciences. 66(1):1-19.
Beygui et al. (2006) "High plasma aldosterone levels on admission are associated with death in patients presenting with acute ST-elevation myocardial infarction," Circulation. 114(24):2604-2610.
Borlongan et al. (2005) "Acute functional effects of cyclosporine-A and methylprednisolone treatment in adult rats exposed to transient ischemic stroke," Life sciences. 76(13):1503-1512.
Bovelli et al. (2010) "Cardiotoxicity of chemotherapeutic agents and radiotherapy-related heart disease: ESMO Clinical Practice Guidelines," Annals of oncology. 21(Supplement 5):v277-v282.
Bullock et al. (1996) "Tissue distribution of messenger ribonucleic acid encoding the rat glucagon-like peptide-1 receptor," Endocrinology. 137(7):2968-2978.
Cung et al. (Sep. 10, 2015) "Cyclosporine before PCI in Patients with Acute Myocardial Infarction," New England Journal of Medicine, the NEJM Massachusetts Medical Society. 373(11):1021-1031.
Dae et al. (2002) "Effect of endovascular cooling on myocardial temperature, infarct size, and cardiac output in human-sized pigs." American Journal of Physiology—Heart and Circulatory Physiology. 282(5):H1584-H1591.
Fröhlich et al. (2013) "Myocardial reperfusion injury: looking beyond primary PCI," European heart journal. 34(23):1714-1722.
Froud et al. (Jul. 1, 2008) "The Use of Exenatide in Islet Transplant Recipients with Chronic Allograft Dysfunction: Safety, Efficacy, and Metabolic Effects," Transplantation. 86(1):36-45.
Göke et al. "Exendin-4 is a high potency agonist and truncated exendin-(9-39)-amide an antagonist at the glucagon-like peptide 1-(7-36)-amide receptor of insulin-secreting beta-cells," Journal of Biological Chemistry. 268(26):19650-19655.
Götberg et al. (2010) "Mild hypothermia reduces acute mortality and improves hemodynamic outcome in a cardiogenic shock pig model;" Resuscitation. 81(9):1190-1196.
Heusch et al. (2010) "Inhibition of mitochondrial permeability transition pore opening: the Holy Grail of cardioprotection," Basic Res Cardiol. 105:151-154.

(Continued)

*Primary Examiner* — James H Alstrum-Acevedo
*Assistant Examiner* — Thea D'Ambrosio
(74) *Attorney, Agent, or Firm* — Brian C. Trinque; Benjamin A. Vaughan; Lathrop Gage LLP

(57) ABSTRACT

The present invention provides a combination comprising at least two of the following: (i) an insulin modulator, (ii) an immunosuppressive agent and (iii) an aldosterone antagonist, for instance a combination comprising at least two of (i) exenatide, or a functional derivative or analog thereof, or a pharmaceutically acceptable salt thereof; (ii) cyclosporine, or a functional derivative or analog thereof, or a pharmaceutically acceptable salt thereof; and (iii) potassium canrenoate, or a functional derivative or analog thereof. Said combinations are suitable for cardioprotection and for treating and/or preventing ischemia and/or reperfusion injury. Further aspects of the invention relate to pharmaceutical products and pharmaceutical compositions comprising said combinations according to the invention, and methods of treatment using the same.

21 Claims, No Drawings

(56) References Cited

OTHER PUBLICATIONS

Hochman et al. (1999) "Early revascularization in acute myocardial infarction complicated by cardiogenic shock," New England Journal of Medicine. 341(9):625-634.
Holmes et al. (1995) "Contemporary reperfusion therapy for cardiogenic shock: the GUSTO-I trial experience," Journal of the American College of Cardiology. 26(3):668-674.
Huang et al. (2011) "Post-cardiac arrest myocardial dysfunction is improved with cyclosporine treatment at onset of resuscitation but not in the reperfusion phase," Resuscitation. 82:S41-S47.
Kern (2015) "Usefulness of Cardiac Arrest Centers—Extending Lifesaving Post-Resuscitation Therapies: The Arizona Experience," Circulation Journal. 79(6):1156-1163.
Kim et al. (Nov. 2013) "Multilayer nanoparticles for sustained delivery of exenatide to treat type 2 diabetes mellitus," Biomaterials. 34(33):8444-9.
Kronick et al. (2015) "Part 4: Systems of Care and Continuous Quality Improvement," Circulation. 132(18):S397-S413.
Lagerqvist et al. (2014) "Outcomes 1 year after thrombus aspiration for myocardial infarction," New England Journal of Medicine. 371(12):1111-1120.
Leger et al. (2011) "Evaluation of cyclosporine A in a stroke model in the immature rat brain." Experimental neurology. 230(1):58-66.
Lepore et al. (Jul. 1, 2016) "Effects of the Novel Long-Acting GLP-1 Agonist, Albiglutide, on Cardiac Function, Cardiac Metabolism, and Exercise Capacity in Patients with Chronic Heart Failure and Reduced Ejection Fraction," JACC: Heart Failure. 4(7):559-566.
Lonborg et al. (Jun. 2, 2012) "Exenatide reduces reperfusion injury in patients with ST-segment elevation myocardial infarction," European Heart Journal. 33(12):1491-1499.
Mandelzweig et al. (2006) "The second Euro Heart Survey on acute coronary syndromes: characteristics, treatment, and outcome of patients with ACS in Europe and the Mediterranean Basin in 2004," European heart journal. 27(19):2285-2293.
Nyström et al. (2004) "Effects of glucagon-like peptide-1 on endothelial function in type 2 diabetes patients with stable coronary artery disease," American Journal of Physiology—Endocrinology and Metabolism. 287(6):E1209-E1215.
Okuda (2006) "A multidisciplinary overview of cardiogenic shock," Shock. 25(6):557-570.
Patel et al. (2013) "Evolution of Reperfusion Therapies for Acute Brain and Acute Myocardial Ischemia." Stroke. 44(1):94-98.
Pitt et al. (Apr. 3, 2003) "Eplerenone, a Selective Aldosterone Blocker, in Patients with Left Ventricular Dysfunction after Myocardial Infarction," New England Journal of Medicine, the NEJM Massachusetts Medical Society. 348(14):1309-1321.
Roger et al. (2012) "AHA statistical update," Heart disease and stroke statistics—2012 Update, A report from the American Heart Association, Circulation. 125:e2-e220.
Schinzel et al. (2005) "Cyclophilin D is a component of mitochondrial permeability transition and mediates neuronal cell death after focal cerebral ischemia," Proceedings of the National Academy of Sciences of the United States of America. 102(34):12005-12010.
Soukoulis et al. (Jun. 5, 2014) "Nonantithrombotic Medical Options in Acute Coronary Syndromes: Old Agents and New Lines on the Horizon," Circulation Research. 114(12):1944-1958.
Steg et al. (2012) "ESC Guidelines for the management of acute myocardial infarction in patients presenting with ST-segment elevation," European heart journal. 33(20):2569-2619.
Struthers (2002) "Aldosterone: cardiovascular assault" American heart journal. 144(5):S2-S7.
Tamargo et al. (Jun. 24, 2011) "Novel therapeutic targets for the treatment of heart failure," Nature Reviews, Drug Discovery. 10(7):536-555.
Wenger (1986) "Synthesis of ciclosporin and analogues: structural and conformational requirements for immunosuppressive activity," Ciclosporin. 38:46-64.
Worner et al. (2013) "Comments on the ESC guidelines for the management of acute myocardial infarction in patients presenting with ST-segment elevation," Revista Española de Cardiologia. 66(01):5-11.
Yellon et al. (Sep. 13, 2007) "Myocardial Reperfusion Injury," N Engl J Med. 357:1121-1135.
Yetgin et al. (2010) "Postconditioning against ischaemia-reperfusion injury: ready for wide application in patients?" Netherlands Heart Journal. 18(8):389-392.
Zannad et al. (2005) "Effect of MR blockade on collagen formation and cardiovascular disease with a specific emphasis on heart failure," Heart failure reviews. 10(1):71-78.
Zweier et al. (2006) "The role of oxidants and free radicals in reperfusion injury," Cardiovascular research. 70(2):181-190.
International Search Report corresponding to International Patent Application No. PCT/IB2016/001582, dated Jan. 30, 2017.
Chou et al. (1984) "Quantitative analysis of dose-effect relationships: the combined effects of multiple drugs or enzyme inhibitors," Adv. Enzyme Regul. 22:27-55.
Timmers et al. (2009) "Exenatide reduces infarct size and improves cardiac function in a porcine model of ischemia and reperfusion injury," J. Am. Coll. Cardiol. 53(6):501-510.
Roubille et al. (Oct. 19, 2013) "New Drug Avenues for Cardioprotection in Patients with Acute Myocardial Infarction," American Journal of Cardiovascular Drugs. 14(1):73-77.
Witten Opinion of the International Preliminary Examining Authority corresponding to International Patent Application No. PCT/IB2016/001582, dated Oct. 26, 2017.
Written Opinion of the International Searching Authority corresponding to International Patent Application No. PCT/IB2016/001582, dated Jan. 30, 2017.

* cited by examiner

COMBINATION

This application is a continuation of International Application No. PCT/IB2016/001582, filed on Nov. 4, 2016, which claims priority to Greece Patent Application No. 20150100486, filed on Nov. 6, 2015, the contents of each of which are incorporated herein by reference in their entirety.

FIELD OF INVENTION

The present invention provides a new combination comprising at least two of the following components: (i) an insulin modulator, (ii) an immunosuppressive agent, and (iii) an aldosterone antagonist, for instance, a combination comprising at least two of (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof. Said combinations are suitable for cardioprotection and/or for treating and/or preventing ischemia and/or reperfusion injury.

Further aspects relate to pharmaceutical products and pharmaceutical compositions comprising said combinations according to the invention, and methods of treatment using the same.

BACKGROUND

Acute myocardial infarction (AMI) is a major cause of mortality and morbidity worldwide. Each year, an estimated 785,000 persons (STEMI 500,000) will have a new AMI in the United States alone and approximately every minute an American will succumb to one (Roger et al., Circulation, 2012, 125: e2-e220). Every sixth man and every seventh woman in Europe will die from myocardial infarction (ESC Guidelines for the management of acute MI in patients presenting with ST-elevation, Eur. Heart J., 2012, 33:2569-2619).

Currently, timely myocardial reperfusion using either thrombolytic therapy or primary percutaneous coronary intervention (PPCI) is the choice therapy for acute ST-segment elevation myocardial infarction (STEMI) patients (Worner et al., Rev Exp Cardiol., 2013, 66: 5-11). These interventions limit myocardial infarct (MI), preserve left-ventricular systolic function and reduce the onset of heart failure.

However, mortality remains substantial in these patients with in-hospital mortality ranging between 6 and 14% (Mandelzweig et al., Eur. Heart J., 2006, 27: 2285-2293).

Furthermore, morbidity remains substantial—MI is the leading cause of chronic heart failure—with about 5 to 6% of patients having a subsequent cardiovascular event by 30 days and re-hospitalisation at 1 year about 2.7%. (Lagerqvist et al., N. Engl. J. Med., 2014, 371:1111-20).

Paradoxically, although myocardial reperfusion is essential for myocardial salvage, providing oxygen and nutrients to the ischemic area comes at a price, as it can in itself induce myocardial injury and cardiomyocyte death—a phenomenon termed "myocardial reperfusion injury", the irreversible consequences of which include microvascular obstruction and myocardial infarction (Yellow and Hausenloy, N. Engl. J. Med., 2007, 357: 1121-1135). It is estimated that ischemia-reperfusion injury is responsible for approximately 50% of the final infarct area (Yetgin et al., Neth. Heart J., 2010; 28, 389-392). Previous attempts to translate cardioprotective therapies (i.e. antioxidants, calcium-channel blockers and anti-inflammatory agents) for reducing reperfusion injury into the clinic have been unsuccessful (Frohlich et al., Eur. Heart J., 2013, 34:1714-1724). There is currently no approved effective therapy for preventing myocardial reperfusion injury in reperfused-STEMI patients, making it an important residual target for cardioprotection.

Pioneering work in the 1990s first implicated the mitochondrial permeability transition pore (MPTP) as a critical mediator of lethal myocardial reperfusion injury. The opening of the MPTP (a non-selective channel of the inner mitochondrial membrane) in the first few minutes of reperfusion leads to mitochondrial $Ca^{2+}$ overload, oxidative stress, restoration of a physiological pH, and ATP depletion (Heusch et al, Basic Res Cardiol, 2010, 105: 151-154). These events induce cardiomyocytes death by uncoupling oxidative phosphorylation.

Alterations in membrane proteins by free radicals are among the important factors in the evolution of myocardial reperfusion damage. Large quantities of reactive oxygen species (ROS) lead to overwhelming of the cellular endogenous antioxidant defenses. This causes, among other effects, the peroxidation of lipid membranes and loss of membrane integrity which results in necrosis and cell death (Zweier and Talukder, Cardiovasc Res, 2006, 70: 181-190). Re-introduction of abundant oxygen at the onset of reperfusion evokes a burst of additional toxic oxygen derivatives, including superoxide anion, hydroxyl radical and peroxynitrite, within the first few minutes of reflow. Moreover, oxidative stress also reduces the bioavailability of nitric oxide (vasodilator compound) at reperfusion, and the administration of NO donors is cardioprotective in animal models.

There is presently a need for an effective treatment of reperfusion injury, particularly myocardial reperfusion injury.

STATEMENT OF INVENTION

The present invention provides new combinations which are cardioprotective and suitable for prevention and/or treatment of reperfusion injury. The combinations and other aspects of the invention provide a treatment which is more efficacious and provides superior clinical outcomes compared to therapies which employ a single active pharmaceutical agent.

A first aspect relates to a combination comprising at least two of the following components: (i) an insulin modulator, (ii) an immunosuppressive agent, and (iii) an aldosterone antagonist.

A second aspect relates to a combination comprising at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof.

A third aspect relates to a pharmaceutical composition comprising at least two of the following components: (i) an insulin modulator, (ii) an immunosuppressive agent, and (iii) an aldosterone antagonist.

A fourth aspect relates to a pharmaceutical composition comprising at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof, and a pharmaceutically acceptable carrier, diluent or excipient.

A fifth aspect relates to a pharmaceutical product comprising at least two of the following components: (i) an insulin modulator, (ii) an immunosuppressive agent, and (iii) an aldosterone antagonist.

A sixth aspect relates to a pharmaceutical product comprising at least two of the following components: (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof.

A seventh aspect relates to a combination or a pharmaceutical composition as defined above for use in the treatment and/or prevention of one or more of ischemia and/or reperfusion injury, ischemic stroke, cardiac arrest, acute myocardial infarction, neonatal asphyxia and cardiogenic shock, or for use in providing cardioprotection against cardiotoxic drugs.

An eighth aspect relates to a pharmaceutical product as defined above for use in the treatment and/or prevention of one or more of ischemia and/or reperfusion injury, ischemic stroke, cardiac arrest, acute myocardial infarction, neonatal asphyxia and cardiogenic shock, or for use in providing cardioprotection against cardiotoxic drugs, wherein the components are for administration simultaneously, sequentially or separately.

A ninth aspect relates to a method of treating and/or preventing one or more of ischemia and/or reperfusion injury, ischemic stroke, cardiac arrest, acute myocardial infarction, neonatal asphyxia and cardiogenic shock, or for providing cardioprotection against cardiotoxic drugs, said method comprising simultaneously, sequentially or separately administering to a subject in need thereof at least two of the following components: (i) an insulin modulator, (ii) an immunosuppressive agent, and (iii) an aldosterone antagonist.

A tenth aspect relates to a method of treating and/or preventing one or more of ischemia and/or reperfusion injury, ischemic stroke, cardiac arrest, acute myocardial infarction, neonatal asphyxia and cardiogenic shock, or for providing cardioprotection against cardiotoxic drugs, said method comprising simultaneously, sequentially or separately administering to a subject in need thereof at least two of the following components: (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof.

An eleventh aspect relates to the use of at least two of the following components: (i) an insulin modulator, (ii) an immunosuppressive agent, and (iii) an aldosterone antagonist, in the manufacture of a medicament for the treatment and/or prevention of one or more of ischemia and/or reperfusion injury, ischemic stroke, cardiac arrest, acute myocardial infarction, neonatal asphyxia and cardiogenic shock, or for providing cardioprotection against cardiotoxic drugs.

A twelfth aspect relates to the use of at least two of the following components: (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof, in the manufacture of a medicament for the treatment and/or prevention of one or more of ischemia and/or reperfusion injury, ischemic stroke, cardiac arrest, acute myocardial infarction, neonatal asphyxia and cardiogenic shock, or for providing cardioprotection against cardiotoxic drugs.

A thirteenth aspect relates to the use of a combination comprising at least two of the following components: (i) an insulin modulator, (ii) an immunosuppressive agent, and (iii) an aldosterone antagonist, for treating and/or preventing ischemia and/or reperfusion injury in an ex vivo organ prior to or during transplantation.

A fourteenth aspect relates to the use of a combination comprising at least two of the following components: (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof, for treating and/or preventing ischemia and/or reperfusion injury in an ex vivo organ prior to or during transplantation.

DETAILED DESCRIPTION

The preferred embodiments set out below are applicable to any of the above-mentioned aspects of the invention as appropriate.

Insulin Modulator

In one embodiment, the combination of the invention comprises an insulin modulator.

As used herein the term "insulin modulator" refers to an agent that is capable of directly or indirectly increasing or decreasing the activity of insulin, which in turn may increase or decrease the insulin-mediated physiological response.

In a preferred aspect, the combination, methods, compositions and uses comprise an an insulin modulator as an essential feature.

In one embodiment, the insulin modulator may be selected from GLP-1 agonists, DPP-4 inhibitors, PPAR agonists, insulin and analogues thereof.

Examples of GLP-1 agonists include exenatide, lixisenatide, albiglutide, liraglutide, taspoglutide and dulaglutide (LY2189265) and pharmaceutically acceptable salts thereof.

Examples of DPP-4 inhibitors include sitagliptin, vildagliptin, saxagliptin, linagliptin anagliptin, teneligliptin, alogliptin, trelagliptin, gemigliptin, dutogliptin and omarigliptin (MK-3102) and pharmaceutically acceptable salts thereof.

Examples of PPAR agonists include clofibrate, gemfibrozil, ciprofibrate, bezafibrate, fenofibrate, saroglitazar, aleglitazar, muraglitazar and tesaglitazar and pharmaceutically acceptable salts thereof.

Examples of insulin analogues include insulin lispro, insulin aspart, insulin glulisine, insulin detemir, insulin degludec, insulin glargine and pharmaceutically acceptable salts thereof.

Accordingly, in one embodiment the insulin modulator may be selected from exenatide, lixisenatide, albiglutide, liraglutide, taspoglutide, dulaglutide (LY2189265), sitagliptin, vildagliptin, saxagliptin, linagliptin anagliptin, teneligliptin, alogliptin, trelagliptin, gemigliptin, dutogliptin, omarigliptin (MK-3102), clofibrate, gemfibrozil, ciprofibrate, bezafibrate, fenofibrate, saroglitazar, aleglitazar, muraglitazar tesaglitazar, insulin lispro, insulin aspart, insulin glulisine, insulin detemir, insulin degludec, insulin glargine and pharmaceutically acceptable salts thereof.

In one embodiment, the insulin modulator is a GLP-1 agonist selected from exenatide, lixisenatide, albiglutide, liraglutide, taspoglutide, dulaglutide (LY2189265) and pharmaceutically acceptable salts thereof. Preferably, the GLP-1 agonist is exenatide.

Exenatide

In one preferred embodiment, the insulin modulator is selected from exenatide and functional derivatives and analogues thereof, and pharmaceutically acceptable salts thereof.

As used herein, the term "exenatide" refers to a 39-mer peptide of the following sequence:

H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$

Exenatide (synonym is exendin 4) is originally isolated from the saliva of the Gila monster, *Heloderma suspectum*, by Eng in 1992. It is an insulin secretagogue with glucoregulatory effects similar to the human peptide glucagon-like peptide-1 (GLP-1).

Exenatide mimics human glucagons-like peptide 1 (GLP-1), a gut incretin hormone that is release in response to nutrient intake (Goke et al., J. Biol. Chem., 1993, 268: 19650-19655). It exerts insulinotropic and insulinomimetic properties via the GLP-1 receptor. GLP-1 receptor is widely expressed in many organs, including heart and vascular endothelium (Bullock et al., Endocrinology, 1996, 137: 2968-2978; Nystrom et al., Am J Physiol Endocrinol Metab, 2004, 287: E1209-E1215). Currently, exenatide is approved as an anti-diabetic drug for the treatment of patients with diabetes mellitus type 2. The recommended dose in this indication is initially 5 µg (mcg) twice daily, increasing to 10 µg twice daily after 1 month based on clinical response.

GLP-1 is ineffective as a therapeutic agent as it has a very short circulating half-life (less than 2 minutes) due to rapid degradation by dipeptidyl peptidase-4. Exenatide is 50% homologous to GLP-1, but has a 2.4 hours half-life in humans as the dipeptidyl peprtidase-4 cleavage site is absent.

Exenatide enhances glucose-dependent insulin secretion by the pancreatic beta-cell, suppresses inappropriately elevated glucagon secretion, and slows gastric emptying. Exenatide is extremely potent, having a minimum effective concentration of 50 pg/mL (12 pM) in humans. Current therapies with exenatide involve twice-daily injections (Byetta®). Also, a slow-release formulation (Bydureon®) has been approved for once-weekly injection.

As used herein a functional analogue of exenatide may refer to a compound having a similar structure, but differing from it in a respect of certain aspects (e.g. it can differ in one or more atoms, functional groups, amino acids residues, or substructures, which are replaced with others). Functional analogues display similar pharmacological properties and may be structurally related.

In one embodiment, the functional derivative or analogue of exenatide is a form of exenatide that is modified so as to extend the half life, for example, conjugates of exenatide.

In one preferred embodiment, the functional derivative or analogue of exenatide is PEGylated exenatide. For example, in one preferred embodiment, the functional derivative or analogue is exenatide mono-PEGylated with 40 kDa PEG. PEGylated exenatide can be prepared by methods known in the art. By way of example, PEGylated forms of exenatide are described in WO 2013/059323 (Prolynx LLC). Exenatide can also be conjugated to other molecules, e.g. proteins.

In one particularly preferred embodiment, the functional derivative or analogue of exenatide is an extended release form, for example, that marketed under the tradename Bydureon®. In another preferred embodiment, the functional derivative or analogue of exenatide is in the form of multilayer nanoparticles for sustained delivery, for example, as described in Kim J Y et al, Biomaterials, 2013 November; 34(33):8444-9.

In another particularly preferred embodiment, the exenatide is in an injectable form such as that marketed under the tradename Byetta®.

As used herein a functional derivative or analogue of exenatide may refer to GLP receptor agonists. Suitable functional derivatives or analogues of exenatide of include lixisenatide, albiglutide, liraglutide, taspoglutide and dulaglutide (LY2189265).

In one embodiment, a functional analogue of exenatide means exenatide modified wherein one or more amino acid residues has been exchanged for another amino acid residue and/or wherein one or more amino acid residues have been deleted and/or wherein one or more amino acid residues have been added and/or inserted.

In one embodiment a functional exenatide analogue comprises less than 10 amino acid modifications (substitutions, deletions, additions (including insertions) and any combination thereof) relative to exenatide, alternatively less than 9, 8, 7, 6, 5, 4, 3 or 2 modifications relative to exenatide.

In one embodiment a functional exenatide analogue comprises 10 amino acid modifications (substitutions, deletions, additions (including insertions) and any combination thereof) relative to exenatide, alternatively 9, 8, 7, 6, 5, 4, 3, 2 or 1 modifications relative to exenatide.

As used herein, functional derivatives of exenatide include salts, isomers, enantiomers, solvates, polymorphs, prodrugs and metabolites thereof.

Immunosuppressive Agent

In one embodiment, the combination of the invention comprises an immunosuppressive agent.

As used herein, the term "immunosuppressive agent" refers to an agent capable of partially or fully suppressing the immune response in a subject.

In one embodiment, the immunosuppressive agent is selected from a glucocorticoid, a cytostatic agent, a cytokine (e.g. interferons, interleukins, chemokines), an immunosuppressive antibody, a calcineurin inhibitor and a TNF binding protein.

In one embodiment, the immunosuppressive agent is selected from an antimetabolite, a calcineurin inhibitor and a TNF binding protein.

Examples of antimetabolites include methotrexate, azathioprine, mercaptopurine and fluorouracil, and pharmaceutically acceptable salts thereof.

Examples of calcineurin inhibitors include cyclosporine, cyclosporine G, N-Methyl-4-isoleucine cyclosporine (also known as NIM811), tacrolimus and pimecrolimus, and pharmaceutically acceptable salts thereof.

Examples of TNF binding proteins include infliximab, etanercept and adalimumab, and pharmaceutically acceptable salts thereof.

Accordingly, in one embodiment, the immunosuppressive agent is selected from methotrexate, azathioprine, mercaptopurine, fluorouracil, cyclosporine, cyclosporine G, N-Methyl-4-isoleucine cyclosporine (also known as NIM811), tacrolimus, pimecrolimus, infliximab, etanercept and adalimumab, and pharmaceutically acceptable salts thereof.

In one embodiment, the immunosuppressive agent is a calcineurin inhibitor. In one embodiment, the calcineurin inhibitor is selected from cyclosporine, cyclosporine G, N-Methyl-4-isoleucine cyclosporine (also known as NIM811), tacrolimus and pimecrolimus, and pharmaceutically acceptable salts thereof. Preferably, the calcineurin inhibitor is cyclosporine.

In another embodiment, the calcineurin inhibitor is selected from cyclosporine, cyclosporine G, and N-Methyl-4-isoleucine cyclosporine (also known as NIM811) and pharmaceutically acceptable salts thereof.

In another embodiment, the calcineurin inhibitor is cyclosporine, or a functional derivative or analogue, or a pharmaceutically acceptable salt thereof.

The invention also encompasses functional derivatives and analogues of the above immunusuppressive agents, particularly those that are modified so as to extend the half life of the agent, for example conjugates of the agent.

Cyclosporine

As used herein, the term "cyclosporine" or "cyclosporin" (also known as cyclosporine A) refers to the natural *Tolypocladium inflatum* cyclic non-ribosomal peptide with the systematic (IUPAC) name of: (3S,6S,9S,12R,15S,18S,21S,24S,30S,33S)-30-Ethyl-33-[(1R,2R,4E)-1-hydroxy-2-methyl-4-hexen-1-yl]-6,9,18,24-tetraisobutyl-3,21-diisopropyl-1,4,7,10,12,15,19,25,28-nonamethyl-1,4,7,10,13,16,19,22,25,28,31-undecaazacyclotritriacontane-2,5,8,11,14,17,20,23,26,29,32-undecone.

Cyclosporine is an immunosuppressant agent used extensively to prevent organ rejection following allogenic transplants. For this indication, the recommended IV dose in this indication is 5 to 6 mg/kg/day initially. It remains, an important tool for managing organ transplantation despite having deleterious effects on renal structure and function. Cyclosporine has also been shown to be effective in the treatment psoriasis, atopic dermatitis, pyoderma gangrenosum, chronic autoimmune urticaria, and rheumatoid arthritis. In these indications the recommended initial dose orally is 2.5 mg/kg/day divided in two administrations daily. However, because of the high degree of toxicity associated with the drug, cyclosporine is typically indicated for severe cases of these conditions. For transplant patients, cyclosporine is generally administered only intermittently, or cyclically, with close monitoring of renal function.

In one embodiment, the present invention relates to a functional derivative or analogue of cyclosporine. In one embodiment, the functional derivative or analogue of cyclosporine is a form of cyclosporine that is modified so as to extend the half life, for example, conjugates of cyclosporine.

As used herein, functional derivatives of cyclosporine include salts, isomers, enantiomers, solvates, polymorphs, prodrugs and metabolites thereof.

As used herein a functional analogue of cyclosporine may refer to a compound having a similar structure, but differing from it in a respect of certain aspects (e.g. it can differ in one or more atoms, functional groups, amino acids residues, or substructures, which are replaced with others). Functional analogues display similar pharmacological properties and may be structurally related.

In one embodiment, the functional derivative or analogue of cyclosporine is selected from cyclosporine G, N-Methyl-4-isoleucine Cyclosporine (also known as NIM811) tacrolimus and pimecrolimus, and pharmaceutically acceptable salts thereof. In another embodiment, the functional derivative or analogue of cyclosporine is selected from cyclosporine G and N-Methyl-4-isoleucine Cyclosporine (also known as NIM811) and pharmaceutically acceptable salts thereof.

Cyclosporine G differs from cyclosporine A in the amino acid 2 position, where an L-norvaline replaces the α-aminobutyric acid. (See generally, Wenger, R. M. 1989, Synthesis of cyclosporine and analogues: structural and conformational requirements for immunosuppressive activity. Progress in Allergy, 38: 46-64).

Aldosterone Antagonist

In one embodiment, the combination of the invention comprises an aldosterone antagonist.

In a preferred aspect, the combination, methods, compositions and uses of the invention comprise an aldosterone antagonist as an essential feature.

Acute myocardial infarction and its subsequent hemodynamic changes lead to complex neurohormonal activation. The renin-angiotensin-aldosterone pathway is one corner stone of such neurohormonal activation. Aldosterone, which is at its highest levels at presentation after acute myocardial infarction, is reported to promote a broad spectrum of deleterious cardiovascular effects including acute endothelial dysfunction, inhibition of NO activity, increased endothelial oxidative stress, increased vascular tone, inhibition of tissue recapture of catecholamines, rapid occurrence of vascular smooth muscle cell and cardiac myocyte necrosis, collagen deposition in blood vessels, myocardial hypertrophy, and fibrosis (Struthers, Am Heart J, 2002, 144: S2-S7; Zannad and Radauceanu, Heart Fail Rev, 2005, 10: 71-78). Furthermore, it has been found to predict poor outcomes (Beygui et al, Circulation, 2006, 114: 2604-2610).

An aldosterone antagonist or an antimineralocorticoid, is a diuretic drug which antagonizes the action of aldosterone at mineralocorticoid receptors. This group of drugs is often used for the management of chronic heart failure. Members of this class are also used in the management of hyperaldosteronism (including Conn's syndrome) and female hirsutism (due to additional antiandrogen actions). Most antimineralocorticoids are steroidal spirolactones.

Antagonism of mineralocorticoid receptors inhibits sodium resorption in the collecting duct of the nephron in the kidneys. This interferes with sodium/potassium exchange, reducing urinary potassium excretion and weakly increasing water excretion (diuresis). In congestive heart failure, aldosterone antagonists are used in addition to other drugs for additive diuretic effect, which reduces edema and the cardiac workload.

Current guidelines recommend the use of mineralocorticoid receptor antagonists, in patients presenting with heart failure post myocardial infarction, based on the results of the EPHESUS trial.

Several studies in animal models of acute myocardial infarction and in the clinic have shown the benefit of aldosterone blockade in the prevention of reperfusion injury and improving heart function in STEMI patient.

Examples of aldosterone antagonists include spironolactone (the first and most widely used member of this class), eplerenone (much more selective than spironolactone on target, but somewhat less potent and efficacious), canrenone and potassium canrenoate, finerenone (non-steroidal and more potent and selective than either eplerenone or spironolactone) and prorenone.

In one particularly preferred embodiment, the aldosterone antagonist is potassium canrenoate.

Some drugs also have antimineralocorticoid effects secondary to their main mechanism of actions. Examples include progesterone, drospirenone, gestodene, and benidipine.

The invention also encompasses functional derivatives and analogues of the aldosterone antagonists, particularly those that are modified so as to extend the half life of the agent, for example, conjugates of aldosterone antagonists.

Potassium Canrenoate

Potassium canrenoate or canrenoate potassium also known as the potassium salt of canrenoic acid, is an aldosterone antagonist of the spirolactone group. Like spironolactone, it is a prodrug, which is metabolized to canrenone in the body. Potassium canrenoate is typically given intravenously at doses ranging between 200 mg/day and 600 mg/day for the treatment of hyperaldosteronism or hypokaliaemia.

Potassium canrenoate has systematic (IUPAC) name potassium 3-[(8R,9S,10R,13S,14S,17R)-17-hydroxy-10,13-dimethyl-3-oxo-2,8,9,11,12,14,15,16 octahydro-1H-cyclopenta[a]phenanthren-17-yl]propanoate, formula $C_{22}H_{29}KO_4$ and the following chemical structure:

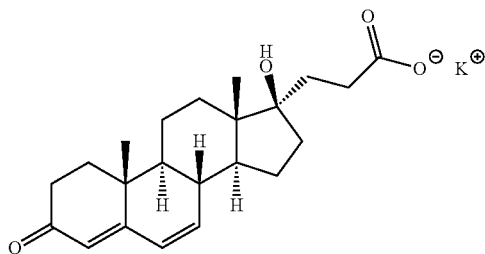

The invention also encompasses functional derivatives and analagues of potassium canrenoate, particularly those that are modified so as to extend the half life of the agent, for example, conjugates of potassium canrenoate.

Combination

In one aspect, the present invention relates to a combination comprising at least two of the following components: (i) an insulin modulator, (ii) an immunosuppressive agent and (iii) an aldosterone antagonist.

The preferred embodiments described below apply mutatis mutandis to other aspects of the invention, including methods, uses, products and compositions.

In one highly preferred embodiment, the combination comprises an insulin modulator and an aldosterone antagonist.

In another preferred embodiment, the combination comprises an insulin modulator and an immunosuppressive agent.

In another embodiment, the combination comprises an immunosuppressive agent, and an aldosterone antagonist.

In another preferred embodiment, the combination comprises (i) an insulin modulator, (ii) an immunosuppressive agent, and (iii) an aldosterone antagonist.

In one embodiment, the insulin modulator is defined according to any of the above-mentioned embodiments of an insulin modulator.

In one embodiment, the immunosuppressive agent is defined according to any of the above mentioned embodiments of an immunosuppressive agent.

In one embodiment, the aldosterone antagonist is defined according to any of the above mentioned embodiments of an aldosterone antagonist.

In another aspect, the present invention relates to a combination comprising at least two of the following components: (i) exenatide, or a functional derivative or analogue, or pharmaceutically acceptable salt thereof; (ii) cyclosporine, or a functional derivative or analogue, or pharmaceutically acceptable salt thereof and (iii) potassium canrenoate, or a functional derivative or analogue.

In one embodiment, the present invention relates to a combination comprising (i) exenatide, or a functional derivative or analogue, or pharmaceutically acceptable salt thereof; and (iii) potassium canrenoate, or a functional derivative or analogue thereof.

In one embodiment, the present invention relates to a combination comprising at least two of the following components: (i) at least one of exenatide, lixisenatide, albiglutide, liraglutide, taspoglutide and dulaglutide (LY2189265), or a pharmaceutically acceptable salt thereof, (ii) at least one of cyclosporine A, cyclosporine G, N-Methyl-4-isoleucine cyclosporine, tacrolimus and pimecrolimus, or a pharmaceutically acceptable salt thereof and (iii) at least one of potassium canrenoate, canrenone, spironolactone, eplerenone, finerenone and prorenone or pharmaceutically acceptable salts thereof, where applicable (e.g. pharmaceutically acceptable salts of canrenone, spironolactone, eplerenone, finerenone and prorenone).

In one embodiment, the present invention relates to a combination comprising (i) at least one of exenatide, lixisenatide, albiglutide, liraglutide, taspoglutide and dulaglutide (LY2189265), or a pharmaceutically acceptable salt thereof, and (iii) at least one of potassium canrenoate, canrenone, spironolactone, eplerenone, finerenone and prorenone or pharmaceutically acceptable salts thereof, where applicable.

In one embodiment, the present invention relates to a combination comprising at least two of the following components: (i) at least one of exenatide, lixisenatide, albiglutide, liraglutide, taspoglutide and dulaglutide (LY2189265), or a pharmaceutically acceptable salt thereof, (ii) at least one of cyclosporine A, cyclosporine G and N-Methyl-4-isoleucine cyclosporine, or a pharmaceutically acceptable salt thereof and (iii) at least one of potassium canrenoate, canrenone, spironolactone, eplerenone, finerenone and prorenone or pharmaceutically acceptable salts thereof, where applicable.

In one embodiment, the present invention relates to a combination of (i) exenatide or a pharmaceutically acceptable salt thereof, and (ii) at least one of cyclosporine A, cyclosporine G, N-Methyl-4-isoleucine cyclosporine, tacrolimus and pimecrolimus, or a pharmaceutically acceptable salt thereof.

In one embodiment, the present invention relates to a combination of (i) exenatide or a pharmaceutically acceptable salt thereof, and (ii) at least one of cyclosporine A, cyclosporine G and N-Methyl-4-isoleucine cyclosporine, or a pharmaceutically acceptable salt thereof.

In one embodiment, the present invention relates to a combination of (i) at least one of exenatide, lixisenatide, albiglutide, liraglutide, taspoglutide and dulaglutide (LY2189265), or a pharmaceutically acceptable salt thereof, and (ii) cyclosporine A or a pharmaceutically acceptable salt thereof.

In one embodiment, the present invention relates to a combination of (i) exenatide or a pharmaceutically acceptable salt thereof, (ii) cyclosporine A or a pharmaceutically acceptable salt thereof, and (iii) potassium canrenoate.

The effect of drug combinations is inherently unpredictable and there is often a propensity for one drug to partially or completely inhibit the effects of the other. The present invention demonstrates that a combination comprising at least two of (i) an insulin modulator, such as exenatide or a functional derivative or analogue or a pharmaceutically acceptable salt thereof, (ii) an immunosuppressive agent, such as cyclosporine or a functional derivative or analogue or a pharmaceutically acceptable salt thereof, and (iii) an aldosterone antagonist, such as potassium canrenoate or a functional derivative or analogue, when administered simultaneously, separately or sequentially, does not lead to any significant or dramatic adverse interaction between the two agents. The unexpected absence of any such antagonistic interaction is critical for clinical applications of the combination.

Moreover, preferred combinations according to the invention surprisingly demonstrate a potentiation of the effect of the individual components, such that the optimal doses for the agents is lower than the doses recommended in the approved indications for these agents, and/or also lower (in all cases but potassium canrenoate) than the doses reported in the literature for reperfusion injury.

In one embodiment, the combinations of the active agents of the present invention (see (i), (ii) and (iii) above) produce an enhanced effect as compared to each drug administered alone.

Furthermore, in another embodiment, the combinations of the active agents of the present invention (see (i), (ii) and (iii) above) produce unexpected synergistic effects, for instance, in the treatment and/or prevention of reperfusion injury, particularly myocardial reperfusion injury.

A combination of two or more drugs may lead to different types of drug interaction. A drug interaction is said to be additive when the combined effect of two drugs equals the sum of the effect of each agent given alone. A drug interaction is said to be synergistic if the combined effect of the two drugs exceeds the effects of each drug given alone (Goodman and Gilmans' "The Pharmacological Basis of Therapeutics", $12^{th}$ Edition).

Combination therapy is an important treatment modality in many disease settings, including cardiovascular disease, cancer and infectious diseases. Recent scientific advances have increased our understanding of the pathophysiological processes that underlie these and other complex diseases. This increased understanding has provided further impetus to develop new therapeutic approaches using combinations of drugs directed at multiple therapeutic targets to improve treatment response, minimize development of resistance, or minimize adverse events. In settings in which combination therapy provides significant therapeutic advantages, there is growing interest in the development of new combinations of two or more drugs.

Advantageously, a synergistic combination may allow for lower doses of each component to be present, thereby decreasing the toxicity of therapy, whilst producing and/or maintaining the same therapeutic effect or an enhanced therapeutic effect. Thus, in a particularly preferred embodiment, each component is present in a sub-therapeutic amount.

The term "sub-therapeutically effective amount" means an amount that is lower than that typically required to produce a therapeutic effect with respect to treatment with each agent alone.

In one embodiment, the present invention relates to a synergistic combination comprising (i) an insulin modulator, and (iii) an aldosterone antagonist.

In one embodiment, the insulin modulator is defined according to any of the above mentioned embodiments of an insulin modulator.

In one embodiment, the aldosterone antagonist is defined according to any of the above mentioned embodiments of an aldosterone antagonist.

In one embodiment the present invention relates to a synergistic combination of (i) at least one of exenatide, lixisenatide, albiglutide, liraglutide, taspoglutide and dulaglutide (LY2189265), or a pharmaceutically acceptable salt thereof, and (iii) at least one of potassium canrenoate, canrenone, spironolactone, eplerenone, finerenone and prorenone or pharmaceutically acceptable salts thereof, where applicable.

In one embodiment, the present invention relates to a synergistic combination of (i) exenatide or a pharmaceutically acceptable salt thereof, and (iii) potassium canrenoate.

In one embodiment, the present invention relates to a synergistic combination of (i) at least one of exenatide, lixisenatide, albiglutide, liraglutide, taspoglutide and dulaglutide (LY2189265), or a pharmaceutically acceptable salt thereof, and (iii) potassium canrenoate.

Additional Active Pharmaceutical Ingredients

In one embodiment, the above described combinations comprise at least one further active pharmaceutical ingredient (API).

In one embodiment, the above described combinations may further comprise at least one further API selected from a beta blocker, a renin-angiotensin inhibitor, a statin (HMG-CoA reductase inhibitor), an inhibitor of platelet activation or aggregation, a phosphodiesterase-3 inhibitor, a calcium sensitizer, an antioxidant and an anti-inflammatory agent.

Examples of beta-blockers include propranolol, metoprolol, bucindolol, carteolol, carvedilol, labetalol, nadolol, oxprenolol, penbutolol, pindolol, sotalol and timolol.

Renin-angiotensin inhibitors include angiotensin converting enzyme inhibitors, angiotensin $AT_1$ receptor inhibitors and renin inhibitors.

Examples of angiotensin converting enzyme inhibitors include captopril, zofenopril, enalapril, ramipril, quinapril, perindopril, lisinopril, benazepril, imidapril, trandolapril, cilazapril, and fosinopril.

Examples of angiotension $AT_1$ receptor antagonists include losartan, irbesartan, olmesartan, candesartan, valsartan, fimasartan and telmisartan.

Examples of renin inhibitors include remikiren and aliskiren.

Examples of calcium sensitizers include levosimendan and analogues thereof.

Examples of statins include atorvastatin, lovastatin, pravastatin, rosuvastatin and simvastatin.

Examples of platelet activation or aggregation inhibitors include prostacyclin (epoprostenol) and analogues and derivatives thereof (eg. treprostinil, iloprost), irreversible cyclooxygenase inhibitors (e.g. Aspirin, Triflusal), adenosine diphosphate (ADP) receptor inhibitors (e.g. Clopidogrel, Prasugrel, Ticagrelor, Ticlopidine), phosphodiesterase inhibitors (e.g. Cilostazol), protease-activated receptor-1 (PAR-1) antagonists (e.g. Vorapaxar), glycoprotein IIB/IIIA inhibitors (e.g. Abciximab, Eptifibatide, Tirofiban), adenosine reuptake inhibitors (e.g. Dipyridamole), and thromboxane inhibitors, including thromboxane synthase inhibitors and thromboxane receptor antagonists (e.g. Terutroban).

Examples of phosphodiesterase-3 (PDE-3) inhibitors include amrinone, milrinone, and analogues thereof.

Examples of antioxidants include ascorbic acid, lipoic acid, glutathione and melatonin.

Examples of anti-inflammatory agents include COX-2 inhibitors (e.g. celecoxib), glucocorticoids (e.g. hydrocortisone), and non-steroidal anti-inflammatory drugs (e.g. ibuprofen).

In one embodiment, the above combinations comprise at least one further API selected from propranolol, metoprolol, bucindolol, carteolol, carvedilol, labetalol, nadolol, oxprenolol, penbutolol, pindolol, sotalol, timolol, captopril, zofenopril, enalapril, ramipril, quinapril, perindopril, lisinopril, benazepril, imidapril, trandolapril, cilazapril, fosinopril, losartan, irbesartan, olmesartan, candesartan, valsartan, fimasartan, telmisartan, remikiren and aliskiren.

In another embodiment, the above combinations comprise at least one further API selected from carvedilol, metoprolol, losartan, irbesartan, olmesartan, candesartan, valsartan, fimasartan telmisartan. captopril, zofenopril, enalapril, ramipril, quinapril, perindopril, lisinopril, benazepril, imidapril, trandolapril, cilazapril, fosinopril, remikiren and aliskiren.

In another embodiment, the above combinations comprise at least one further API selected from carvedilol and metoprolol.

Pharmaceutically Acceptable Salts

The active pharmaceutical agents of the present invention can be present as pharmaceutically acceptable salts.

Pharmaceutically acceptable salts of the agents of the invention include suitable acid addition or base salts thereof. A review of suitable pharmaceutical salts may be found in Berge et al., J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C1-C4)-alkyl- or aryl-sulfonic acids which are unsubstituted or substituted (for example, by a halogen) such as methane- or p-toluene sulfonic acid.

Enantiomers/Tautomers

The invention also includes where appropriate all enantiomers and tautomers of the active pharmaceutical agents. The man skilled in the art will recognise compounds that possess optical properties (one or more chiral carbon atoms) or tautomeric characteristics. The corresponding enantiomers and/or tautomers may be isolated/prepared by methods known in the art.

Stereo and Geometric Isomers

Some of the active pharmaceutical agents of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the active pharmaceutical agents or pharmaceutically acceptable salts thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the active pharmaceutical agents of the present invention. The terms used in the claims encompass these forms.

Polymorphs

The invention furthermore relates to active pharmaceutical agents of the present invention in their various crystalline forms, polymorphic forms and (an)hydrous forms. It is well established within the pharmaceutical industry that chemical compounds may be isolated in any of such forms by slightly varying the method of purification and or isolation from the solvents used in the synthetic preparation of such compounds.

Pharmaceutical Compositions

In another aspect, the present invention relates to a pharmaceutical composition comprising a combination comprising at least two of the following components: (i) an insulin modulator, (ii) an immunosuppressive agent and (iii) an aldosterone antagonist; and a pharmaceutically acceptable carrier, diluent or excipient.

In another aspect, the present invention relates to a pharmaceutical composition comprising a combination comprising at least two of the following components: (i) exenatide, or a functional derivative or analogue, or a pharmaceutically acceptable salt thereof; (ii) cyclosporine, or a functional derivative or analogue, or a pharmaceutically acceptable salt thereof and (iii) potassium canrenoate, or a functional derivative or analogue; and a pharmaceutically acceptable carrier, diluent or excipient.

Even though the compounds of the present invention (including their pharmaceutically acceptable salts) can be administered alone, they will generally be administered in admixture with a pharmaceutical carrier, excipient or diluent, particularly for human therapy. The pharmaceutical compositions may be for human or non-human animal usage in human and veterinary medicine respectively.

Examples of such suitable excipients for the various different forms of pharmaceutical compositions described herein may be found in the "Handbook of Pharmaceutical Excipients", $2^{nd}$ Edition, (1994), edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

The choice of pharmaceutical carrier, excipient or diluent can be selected with regard to the intended route of administration and standard pharmaceutical practice. Examples of routes of administration include parenteral (e.g., intravenous, intramuscular, intradermal, intraperitoneal or subcutaneous), oral, inhalation, transdermal (topical), intraocular, iontophoretic, and transmucosal administration.

In one embodiment, the pharmaceutical composition is for parenteral administration (e.g., intravenous, intraarterial, intrathecal, intramuscular, intradermal, intraperitoneal or subcutaneous). Preferably, the compositions are prepared from sterile or sterilisable solutions.

In another embodiment, the pharmaceutical composition is for intravenous, intramuscular, or subcutaneous administration.

In another embodiment, the pharmaceutical composition is for intravenous administration.

Solutions or suspension used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl-alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ or phosphate buffered saline (PBS). In all cases, a composition for parenteral administration must be sterile and should be fluid to the extent that easy syringeability exists. It should be stable under the conditions of manufacture and storage and must be preserved against the contaminating action of microorganisms such as bacteria and fungi.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compounds into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof. The invention also encompasses liposomal and nanoparticulate formulations comprising the active agents. Such formulations, along with methods for their preparation, will be familiar to a person of ordinary skill in the art.

Pharmaceutical Products

In another aspect, the present invention relates to a pharmaceutical product comprising at least two of the following components: (i) an insulin modulator, (ii) an immunosuppressive agent and (iii) an aldosterone antagonist.

In another aspect, the present invention relates to a pharmaceutical product comprising at least two of the following components: (i) exenatide, or a functional derivative or analogue, or pharmaceutically acceptable salt thereof; (ii) cyclosporine, or a functional derivative or analogue, or pharmaceutically acceptable salt thereof and (iii) potassium canrenoate, or a functional derivative or analogue.

In one embodiment, the pharmaceutical product is a kit of parts containing all necessary equipment (e.g., vials of drug, vials of diluent, syringes and needles) for a treatment course.

In one embodiment, the kit comprises separate containers for each active agent. Said containers may be ampoules, disposable syringes or multiple dose vials.

In another embodiment, the kit comprises a container which comprises a combined preparation of each active agent.

The kit may further comprise instructions for the treatment and/or prevention of reperfusion injury.

Medical Uses

In one aspect, the present invention relates to a combination comprising at least two of the following components: (i) an insulin modulator (ii) an immunosuppressive agent, and (iii) an aldosterone antagonist for use in the treatment and/or prevention of one or more of ischemia and/or reperfusion injury, ischemic stroke, cardiac arrest, acute myocardial infarction, neonatal asphyxia and cardiogenic shock, or for use in providing cardioprotection against cardiotoxic drugs.

In one aspect, the present invention relates to a combination comprising at least two of the following components: (i) exenatide, or a functional derivative or analogue, or pharmaceutically, acceptable salt thereof; (ii) cyclosporine, or a functional derivative or analogue, or pharmaceutically acceptable salt thereof; and (iii) potassium canrenoate, or a functional derivative or analogue, for use in the treatment and/or prevention of one or more of ischemia and/or reperfusion injury, ischemic stroke, cardiac arrest, acute myocardial infarction, neonatal asphyxia and cardiogenic shock, or for use in providing cardioprotection against cardiotoxic drugs.

In another aspect, the present invention relates to a pharmaceutical composition comprising a combination comprising at least two of the following components: (i) an insulin modulator, (ii) an immunosuppressive agent and (iii) an aldosterone antagonist for use in the treatment and/or prevention of one or more of ischemia and/or reperfusion injury, ischemic stroke, cardiac arrest, acute myocardial infarction, neonatal asphyxia and cardiogenic shock, or for use in providing cardioprotection against cardiotoxic drugs.

In another aspect, the present invention relates to a pharmaceutical composition comprising a combination comprising at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue, for use in the treatment and/or prevention of one or more of ischemia and/or reperfusion injury, ischemic stroke, cardiac arrest, acute myocardial infarction, neonatal asphyxia and cardiogenic shock, or for use in providing cardioprotection against cardiotoxic drugs.

In another aspect, the present invention relates to a pharmaceutical product comprising at least two of the following components: (i) an insulin modulator, (ii) an immunosuppressive agent and (iii) an aldosterone antagonist, for use in the treatment and/or prevention of one or more of ischemia and/or reperfusion injury, ischemic stroke, cardiac arrest, acute myocardial infarction, neonatal asphyxia and cardiogenic shock, or for use in providing cardioprotection against cardiotoxic drugs, wherein the components are for administration simultaneously, sequentially or separately.

In another aspect, the present invention relates to a pharmaceutical product comprising at least two of the following components: (i) exenatide, or a functional derivative or analogue, or pharmaceutically acceptable salt thereof; (ii) cyclosporine, or a functional derivative or analogue, or pharmaceutically acceptable salt thereof and (iii) potassium canrenoate, or a functional derivative or analogue, for use in the treatment and/or prevention of one or more of ischemia and/or reperfusion injury, ischemic stroke, cardiac arrest, acute myocardial infarction, neonatal asphyxia and cardiogenic shock, or for use in providing cardioprotection against cardiotoxic drugs, wherein the components are for administration simultaneously, sequentially or separately.

In another aspect, the present invention relates to use of at least two of the following components: (i) an insulin modulator and (ii) an immunosuppressive agent and (iii) an aldosterone antagonist in the manufacture of a medicament for the treatment and/or prevention of one or more of ischemia and/or reperfusion injury, ischemic stroke, cardiac arrest, acute myocardial infarction, neonatal asphyxia and cardiogenic shock or for providing cardioprotection against cardiotoxic drugs.

In another aspect, the present invention relates to use of at least two of the following components: (i) exenatide, or a functional derivative or analogue, or pharmaceutically acceptable salt thereof; (ii) cyclosporine, or a functional derivative or analogue, or pharmaceutically acceptable salt thereof and (iii) potassium canrenoate, or a functional derivative or analogue thereof in the manufacture of a medicament for the treatment and/or prevention of one or more of ischemia and/or reperfusion injury, ischemic stroke, cardiac arrest, acute myocardial infarction, neonatal asphyxia and cardiogenic shock, or for providing cardioprotection against cardiotoxic drugs.

In one embodiment, the present invention relates to a combination comprising at least two of the following components: (i) an insulin modulator, (ii) an immunosuppressive agent and (iii) an aldosterone antagonist for use in the treatment and/or prevention of reperfusion injury.

In one embodiment, the present invention relates to a combination comprising at least two of the following components: (i) exenatide, or a functional derivative or analogue, or pharmaceutically acceptable salt thereof; (ii) cyclosporine, or a functional derivative or analogue, or pharmaceutically acceptable salt thereof and (iii) potassium canrenoate, or a functional derivative or analogue thereof, for use in the treatment and/or prevention of reperfusion injury.

In another embodiment, the present invention relates to a pharmaceutical composition comprising a combination comprising at least two of the following components: (i) an insulin modulator (ii) an immunosuppressive agent and (iii) an aldosterone antagonist for use in the treatment and/or prevention of reperfusion injury.

In another embodiment, the present invention relates to a pharmaceutical composition comprising a combination comprising at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof, for use in the treatment and/or prevention of reperfusion injury.

In another embodiment, the present invention relates to a pharmaceutical product comprising at least two of the following components: (i) an insulin modulator, (ii) an immunosuppressive agent and (iii) an aldosterone antagonist for use in the treatment and/or prevention of reperfusion injury, wherein the components are for administration simultaneously, sequentially or separately.

In another embodiment, the present invention relates to a pharmaceutical product comprising at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof, for use in the treatment and/or prevention of reperfusion injury, wherein the components are for administration simultaneously, sequentially or separately.

In another embodiment, the present invention relates to use of at least two of the following components: (i) an insulin modulator, (ii) an immunosuppressive agent and (iii) an aldosterone antagonist in the manufacture of a medicament for the treatment and/or prevention of reperfusion injury.

In another embodiment, the present invention relates to use of at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof in the manufacture of a medicament for the treatment and/or prevention of reperfusion injury.

In one embodiment, the present invention relates to a combination comprising at least two of the following components: (i) an insulin modulator, (ii) an immunosuppressive agent and (iii) an aldosterone antagonist for use in the treatment and/or prevention of ischemia.

In one embodiment, the present invention relates to a combination comprising at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof, for use in the treatment and/or prevention of ischemia.

In another embodiment, the present invention relates to a pharmaceutical composition comprising a combination comprising at least two of the following components: (i) an insulin modulator, (ii) an immunosuppressive agent and (iii) an aldosterone antagonist for use in the treatment and/or prevention of ischemia.

In another embodiment, the present invention relates to a pharmaceutical composition comprising a combination comprising at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof, for use in the treatment and/or prevention of ischemia.

In another embodiment, the present invention relates to a pharmaceutical product comprising at least two of the following components: (i) an insulin modulator, (ii) an immunosuppressive agent and (iii) an aldosterone antagonist for use in the treatment and/or prevention of ischemia, wherein the components are for administration simultaneously, sequentially or separately.

In another embodiment, the present invention relates to a pharmaceutical product comprising at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof, for use in the treatment and/or prevention of ischemia, wherein the components are for administration simultaneously, sequentially or separately.

In another embodiment, the present invention relates to use of at least two of the following components: (i) an insulin modulator, (ii) an immunosuppressive agent and (iii) an aldosterone antagonist in the manufacture of a medicament for the treatment and/or prevention of ischemia.

In another embodiment, the present invention relates to use of at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof, in the manufacture of a medicament for the treatment and/or prevention of ischemia.

As used herein, the term "reperfusion injury" refers to the damage to tissue caused when blood supply returns to the tissue after a period of ischemia. The absence of oxygen and nutrients from blood creates a condition in which the restoration of circulation results in inflammation, mitochondrial dysfunction and oxidative damage through the induction of oxidative stress rather than restoration of normal function. Reperfusion injury can occur after a spontaneously occurring event, e.g., arterial blockage, or a planned event, e.g., any of a number of surgical interventions. Myocardial reperfusion injury can occur, for example, after myocardial infarction or as a result of heart transplantation.

In one embodiment, the ischemia and/or reperfusion injury may be ischemia and/or reperfusion injury of the brain, heart, lung, kidney, or other organ/tissue susceptible to ischemia and/or reperfusion injury.

In one embodiment, the ischemia and/or reperfusion injury is ischemia and/or reperfusion injury of the heart, preferably myocardial ischemia and/or myocardial reperfusion injury.

The insulin modulator, the immunosuppressive agent and aldosterone antagonist may be for administration simultaneously, sequentially or separately (as part of a dosing regimen).

Exenatide or functional derivatives or analogues or pharmaceutically acceptable salts thereof, cyclosporine or functional derivatives or analogues or pharmaceutically acceptable salts thereof, and potassium canrenoate or functional derivatives or analogues thereof, may be for administration simultaneously, sequentially or separately (as part of a dosing regimen).

As used herein, "simultaneously" is used to mean that the two agents are administered concurrently.

As used herein, "sequentially" is used to mean that the active agents are not administered concurrently, but one after the other. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between administrations of the components will vary depending on the exact nature of the components, the interaction there between, and their respective half-lives.

In contrast to "sequentially", "separately" is used herein to mean that the gap between administering one agent and the other is significant i.e. the first administered agent may no longer be present in the bloodstream in a therapeutically effective amount when the second agent is administered.

In one embodiment, the components of the combination are for simultaneous administration.

Methods of Treatment

In another aspect, the present invention relates to a method of treating and/or preventing ischemia and/or reperfusion injury, said method comprising simultaneously, sequentially or separately administering to a subject at least two of the following components: (i) an insulin modulator, (ii) an immunosuppressive agent and (iii) an aldosterone antagonist.

In another aspect, the present invention relates to a method of treating and/or preventing ischemia and/or reperfusion injury, said method comprising simultaneously, sequentially or separately administering to a subject in need thereof at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof.

In one embodiment, the present invention relates to a method of treating and/or preventing reperfusion injury, said method comprising simultaneously, sequentially or separately administering to a subject in need thereof at least two of the following components: (i) an insulin modulator, (ii) an immunosuppressive agent and (iii) an aldosterone antagonist.

In one embodiment, the present invention relates to a method of treating and/or preventing reperfusion injury, said method comprising simultaneously, sequentially or separately administering to a subject in need thereof at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof.

In another embodiment, the present invention relates to a method of treating and/or preventing ischemia, said method comprising simultaneously, sequentially or separately administering to a subject in need thereof at least two of the following components: (i) an insulin modulator, (ii) an immunosuppressive agent and (iii) an aldosterone antagonist.

In another embodiment, the present invention relates to a method of treating and/or preventing ischemia, said method comprising simultaneously, sequentially or separately administering to a subject in need thereof at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof.

In one embodiment, the method relates to treating and/or preventing ischemia and/or reperfusion injury of the brain, heart, lung, kidney, or other organ/tissue susceptible to ischemia and/or reperfusion injury.

In one embodiment, the method relates to treating and/or preventing reperfusion injury of the brain, heart, lung, kidney, or other organ/tissue susceptible to reperfusion injury.

In one embodiment, the method relates to treating and/or preventing ischemia of the brain, heart, lung, kidney, or other organ/tissue susceptible to ischemia.

In another embodiment, the method relates to treating and/or preventing ischemia and/or reperfusion injury of the heart, preferably myocardial ischemia and/or myocardial reperfusion injury.

In another embodiment, the method relates to treating and/or preventing reperfusion injury of the heart, preferably myocardial reperfusion injury.

In one particularly preferred embodiment, the method relates to treating and/or preventing acute myocardial infarction. Acute myocardial infarction is one of the most common clinical indications of reperfusion injury.

In another embodiment, the method relates to treating and/or preventing neonatal asphyxia.

Neonatal asphyxia (or perinatal asphyxia) is the medical condition resulting from deprivation of oxygen to a newborn infant that lasts long enough during the birth process to cause physical harm, usually to the brain. The most common cause of neonatal asphyxia is a drop in maternal blood pressure or other interference to the blood flow to the infant's brain during delivery, for example, due to inadequate circulation or perfusion, impaired respiratory effort, or inadequate ventilation.

Neonatal asphyxia can cause hypoxic damage to most of the infant's organs (heart, lungs, liver, gut, kidneys), but brain damage is of most concern and perhaps the least likely to quickly or completely heal. In more pronounced cases, an infant will survive, but with damage to the brain manifested as either mental, such as developmental delay or intellectual disability, or physical, such as spasticity. An infant suffering severe perinatal asphyxia usually has poor color (cyanosis), perfusion, responsiveness, muscle tone, and respiratory effort. Extreme degrees of asphyxia can cause cardiac arrest and death. Neonatal asphyxia occurs in 2 to 10 per 1000 newborns that are born at term, and in higher instances for those that are born prematurely. WHO estimates that 4 million neonatal deaths occur yearly due to birth asphyxia, representing 38% of deaths of children under 5 years of age.

In another embodiment, the method relates to treating and/or preventing ischemia of the heart, preferably myocardial ischemia.

In one embodiment, the subject is a mammal, more preferably a human.

In one embodiment, the method comprises parenterally (e.g., intravenously, intramuscularly, intradermally, intraperitoneally or subcutaneously) administering the components to the subject.

In another embodiment, the method comprises intravenously, intramuscularly, or subcutaneously administering the components to the subject.

In another embodiment, the method comprises intravenously administering (the components to the subject.

Each component can be administered by the same or different route to the other components. Preferably, the components are administered by the same route.

In one embodiment, the claimed combinations are administered to a donor subject and/or a recipient subject prior to and/or during and/or after heart transplant. For example, in some embodiments the combination may be administered to a first subject from which the heart organ will be removed for transplantation into a second subject. Additionally or alternatively, in some embodiments, the combination is administered to the extracted heart organ, prior to introduction into the second subject. Additionally or alternatively, in some embodiments, the combination therapy is administered to the second subject before, during and/or after heart transplant.

In one embodiment, the claimed combinations are for administration to a subject with cardiogenic shock. Cardiogenic shock is a life-threatening medical condition resulting from an inadequate circulation of blood due to primary failure of the ventricles of the heart to function effectively. The condition occurs in 2-10% of patients hospitalized due to myocardial infarction and is the main cause of death among these patients (Holmes et al, 1995, J Am Coll Cardiol, 26: 668-674). More specifically, cardiogenic shock is the result of a complex process with failure of oxygen delivery, generalized ATP deficiency, and multi-organ dysfunction initiated by cardiac pump failure (Okuda, 2006, Shock, 25: 557-570). As this is a type of circulatory shock, there is insufficient perfusion of tissue to meet the demands for oxygen and nutrients. The condition involves increasingly more pervasive cell death from oxygen starvation (hypoxia) and nutrient starvation (e.g. low blood sugar). Because of this, it may lead to cardiac arrest (or circulatory arrest), which is an abrupt stopping of cardiac pump function (as well as stopped respiration and a loss of consciousness). Cardiogenic shock is defined by sustained low blood pressure with tissue hypoperfusion despite adequate left ventricular filling pressure. Signs of tissue hypoperfusion include low urine production (<30 mL/hour), cool extremities, and altered level of consciousness. Several large trials have demonstrated that coronary revascularization is the most important strategy to improve patient survival (Hochman et al, 1999, N Engl J Med, 341: 625-634). However, patients who develop cardiogenic shock despite acute revascularization have a poor prognosis, likely due to reperfusion injury and considered to be associated to the resulted infarct size. Indeed, hypothermia has shown to offer tissue protection in myocardial ischemia, and preclinical studies have shown beneficial results in reducing infarct size in experimentally induced myocardial infarction (Dae et al, 2002, Am J Physiol Heart Circ Physiol, 282: H1584-H1591). Accordingly, in a pig model mild therapeutic hypothermia reduced acute mortality in cardiogenic shock, and improved hemodynamic parameters (Gotberg et al, 2010, Resuscitation, 81: 1190-1196).

In one embodiment, the claimed combinations are for administration to a subject with cardiac arrest. Cardiac arrest is a sudden stop in effective blood flow due to the failure of the heart to contract effectively. The most common cause of cardiac arrest is coronary artery disease. Treatment for cardiac arrest is immediate cardiopulmonary resuscitation (CPR) and if a shockable rhythm is present defibrillation. In the United States cardiac arrest outside of hospital occurs in about 13 per 10,000 people per year (326,000 cases). In hospital cardiac arrest occurs in an additional 209,000 (Kronic et al, Circulation, 2015, 132: S397-S413). In addition to providing high quality cardiopulmonary resuscitation, optimizing the management for post-cardiac arrest syndrome is critically important for improving the long term outcome for cardiac arrest patients. Within this syndrome ("post-cardiac arrest syndrome") there are 3 major areas of emphasis: (1) post-cardiac arrest brain injury; (2) post-cardiac arrest myocardial dysfunction and reperfusion injury; and (3) systemic ischemia-reperfusion response. It is now clear that post-resuscitation care can affect long-term survival and the myocardial and neurological recovery and function of survivors (Kern, 2015, Circ J, 79: 1156-1163). The inhibition of mitochondrial permeability transition pore (MPTP) opening during ischemia-reperfusion can ameliorate injuries in heart and other systemic organs. Indeed, it has been shown in an animal model of cardiac arrest that post-cardiac arrest myocardial dysfunction and survival can be improved by cyclosporine treatment (Huang et al, 2011, Resuscitation, 82S: S41-S47).

In one embodiment, the claimed combinations are for administration to a subject with stroke. Stroke is when poor blood flow to the brain results in cell death. There are two main types of stroke: ischemic, due to lack of blood flow, and hemorrhagic, due to bleeding. They result in part of the brain not functioning properly. Signs and symptoms of a stroke may include an inability to move or feel on one side of the body, problems understanding or speaking, feeling like the world is spinning, or loss of vision to one side among others. An ischemic stroke is typically caused by blockage of a blood vessel. Ischemic stroke treatment includes surgery to open up (reperfusion) the arteries to the brain in those with problematic narrowing. An ischemic stroke, if detected within three to four and half hours, may be treatable with a medication that can break down the clot. In 2013, stroke was the second most frequent cause of death after coronary artery disease, accounting for 6.4 million deaths (12% of the total).

Ischemic stroke and acute myocardial infarction require emergency reperfusion in order to improve functional outcome (Patel and Saver, 2013, Stroke, 44: 94-98). Intravenous tissue-type plasminogen activator has long been the only reperfusion therapy with proven clinical benefit in patients with acute ischemic stroke. As it happens in acute myocardial infarction, endovascular methods restoring reperfusion in acute ischemic stroke may expose patients to increased ischemic/reperfusion injury, thereby hampering the benefit of recanalization by promoting hemorrhagic transformation and severe vasogenic edema both considering as markers of reperfusion injury (Bai and Lyden, 2015, Int J Stroke, 10: 143-152). Experimental evidence indicates that brain ischemic reperfusion injury (as happens in myocardial reperfusion injury) may be attenuated by ischemic pre- and post-conditioning. In addition, experimental evidence suggests that mitochondrial permeability transition pore (MPTP) plays a critical role both in myocardial and brain ischemic reperfusion injury (Schinzel et al, 2005, Proc Natl Acad Sci USA, 102: 12005-12010) and cyclosporine A, (a MPTP opening inhibitor) may prevent brain ischemic reperfusion injury in animal models (Leger et al, 2011, Exp Neurol, 230: 58-66; Borlongan et al, 2005, Life Sci, 76: 1503-1512).

In one embodiment the subject is at risk of (or susceptible to) vessel occlusion injury or cardiac ischemia-reperfusion injury.

In one embodiment, the claimed combinations are for use in, or methods of, providing cardioprotection in a subject against the cardiotoxic effects of drugs (e.g. anthracyclins). Examples of cardiotoxic drugs are described in Bovelli et al (Annals of Oncology 21 (Supplement 5): v277-v282, 2010).

As used herein, the term "cardioprotection" refers to protecting the heart, for example, by preventing, reducing or delaying myocardial injury. Cardiotoxic drugs include drugs associated with cardiac heart failure, drugs associated with ischaemia or thromboembolism, drugs associated with hypertension, drugs associated with other toxic effects such as tamponade and endomyocardial fibrosis, haemorrhagic myocarditis, bradyarrhythmias, Raynaud's phenomenon, autonomic neuropathy, QT prolongation or torsades de pointes, or pulmonary fibrosis. Examples of cardiotoxic drugs include anthracyclines/anthraquinolones, cyclophosphamide, Trastuzumab and other monoclonal antibody-based tyrosine kinase inhibitors, antimetabolites (fluorouracil, capecitabine), antimicrotubule agents (paclitaxel, docetaxel), cisplatin, thalidomide, bevacizumab, sunitinib, sorafenib, busulfan, paclitaxel, vinblastine, bleomycin, vincristine, arsenic trioxide, bleomycin, methotrexate.

In one embodiment, the components are administered simultaneously.

In one embodiment, the (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof are administered simultaneously.

In one embodiment, the components are administered sequentially or separately.

For a three component combination, all three components can be administered simultaneously, or any two components can be administered simultaneously, with the third component administered separately or sequentially. Alternatively, all three components can be administered in any order separately or sequentially.

In one embodiment, (i) is administered prior to sequentially or separately administering (ii).

In another embodiment, (ii) is administered prior to sequentially or separately administering (i).

In one embodiment, (i) is administered prior to sequentially or separately administering (iii).

In one embodiment, (iii) is administered prior to sequentially or separately administering (i).

In one embodiment, the (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof, are administered sequentially or separately.

In one embodiment, the components are each administered in a therapeutically effective amount with respect to the individual components.

In one embodiment, the (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof, are each administered in a therapeutically effective amount with respect to the individual components.

As used herein, the term "therapeutically effective amount" refers to a quantity sufficient to achieve a desired therapeutic and/or prophylactic effect, e.g., an amount which results in the prevention of, or a decrease in, ischemia and/or reperfusion injury or one or more symptoms associated with ischemia and/or reperfusion injury.

In the context of therapeutic or prophylactic applications, the amount of a composition administered to the subject will depend on the type and severity of the disease and on the characteristics of the individual, such as general health, age, sex, body, weight and tolerance to drugs. It will also depend on the degree severity and type of disease. The skilled artisan will be able to determine appropriate dosages depending on these and other factors. The composition can also be administered in combination with one or more additional therapeutic agents.

In one embodiment, the components are each administered in a sub-therapeutically effective amount with respect to the individual components.

In one embodiment, the (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof, are each administered in a sub-therapeutically effective amount with respect to the individual components.

In one embodiment, the components are administered prior to reperfusion the subject.

In one embodiment, the (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof, are administered prior to reperfusion the subject.

In one embodiment, the components are administered during reperfusion of the subject.

In one embodiment, the (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof, are administered during reperfusion of the subject.

In one embodiment, the components are administered after reperfusion of the subject.

In one embodiment, the (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof, are administered after reperfusion of the subject.

In one embodiment, the components are administered prior to and/or during. and/or after reperfusion of the subject.

In one embodiment, the (i) exenatide, or a functional derivative or analogue, or pharmaceutically acceptable salt thereof; (ii) cyclosporine, or a functional derivative or analogue, or pharmaceutically acceptable salt thereof, and (iii) potassium canrenoate, or a functional derivative or analogue thereof, are administered prior to, during and after reperfusion of the subject.

In some embodiments of the method, the subject is administered (i) continuously before, during, and after reperfusion of the subject and is administered (ii) as a bolus dose prior to reperfusion.

In some embodiments of the method, the subject is administered (ii) continuously before, during, and after reperfusion of the subject and is administered (i) as a bolus dose prior to reperfusion.

In some embodiments of the method, the subject is administered (i), (ii) and (iii) continuously before, during, and after reperfusion of the subject.

In some embodiments of the method, additional administration of one or more of the components may occur after reperfusion. Preferably, this repeat administration is carried out at least twice, more preferably from 2 to 100 times, or can be in the form of continuous infusion.

In some embodiments of the method, the subject is administered the components as a bolus dose prior to reperfusion.

In some embodiments of the method, the subject is administered the components as a bolus dose during reperfusion.

In some embodiments of the method, the subject is administered the components as a bolus dose after reperfusion.

As used herein "reperfusion" is the restoration of blood flow to any organ or tissue in which the flow of blood is decreased or blocked. For example, blood flow can be restored to any organ or tissue affected by ischemia or hypoxia. The restoration of blood flow (reperfusion) can occur by any method known to those in the art. For instance, reperfusion of ischemic cardiac tissues may arise from revascularization.

In one embodiment, reperfusion is achieved via a revascularization procedure. In one embodiment, the revascularization procedure is selected from the group consisting of: percutaneous coronary intervention; balloon angioplasty; insertion of a bypass graft; insertion of a stent; directional coronary atheroctomy; treatment with a one or more thrombolytic agent(s); and removal of an occlusion.

In one embodiment, the one or more thrombolytic agents are selected from the group consisting of: tissue plasminogen activator; urokinase; prourokinase; streptokinase; acylated form of plasminogen; acylated form of plasmin; and acylated streptokinase-plasminogen complex.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In one highly preferred embodiment of the invention, the dose of the insulin modulator (e.g. exenatide) in the combination is generally lower than the dose typically used in monotherapy in the context of its currently approved therapies, and/or lower than the general doses reported in the reperfusion injury literature.

In one highly preferred embodiment of the invention, the dose of the immunosuppressive agent (e.g. cyclosporine) in the combination is generally lower than the dose typically used in monotherapy in the context of its currently approved therapies, and/or lower than the general doses reported in the reperfusion injury literature.

When used in the presently claimed combinations, exenatide is preferably administered in a dose of from about 0.001 to about 1.5 µg/kg, more preferably from about 0.005 to about 0.15 µg/kg.

When used in the presently claimed combinations, potassium canrenoate is preferably administered in a dose of from about 0.03 to about 10, preferably from about 1 to about 10 mg/kg, more preferably, from about 1 to about 5 mg/kg, even more preferably, from about 1 to about 3 mg/kg.

When used in the presently claimed combinations, cyclosporine is preferably administered in a dose of from about 0.001 to about 10 mg/kg, more preferably from about 0.01 to about 5 mg/k, even more preferably from about 0.01 to about 2.5 mg/kg.

In one highly preferred embodiment, the combination is a fixed dose combination comprising predetermined dosages of the respective components (e.g. about 0.005 to about 0.05 µg/kg exenatide and from about 1 to about 3 mg/kg potassium canrenoate, more preferably, about 0.05 µg/kg exenatide and 1 mg/kg potassium canrenoate).

Non-Therapeutic Use

In another aspect, the present invention relates to use of a combination comprising at least two of the following components: (i) an insulin modulator, (ii) an immunosuppressive agent and (iii) an aldosterone antagonist for treating and/or preventing ischemia and/or reperfusion injury in an ex vivo organ prior to or during transplantation.

In another aspect, the present invention relates to use of a combination comprising at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof for treating and/or preventing ischemia and/or reperfusion injury in an ex vivo organ prior to or during transplantation.

In one embodiment, the present invention relates to use of a combination comprising at least two of the following components: (i) an insulin modulator, (ii) an immunosuppressive agent and (iii) an aldosterone antagonist for treating and/or preventing reperfusion injury in an ex vivo organ prior to or during transplantation.

In one embodiment, the present invention relates to use of a combination comprising at least two of the following components: (i) exenatide, or a functional derivative or analogue, or a pharmaceutically acceptable salt thereof; (ii) cyclosporine, or a functional derivative or analogue, or a pharmaceutically acceptable salt thereof; and (iii) potassium canrenoate, or a functional derivative or analogue thereof for treating and/or preventing reperfusion injury in an ex vivo organ prior to or during transplantation.

In one embodiment, the present invention relates to use of a combination comprising at least two of the following components: (i) an insulin modulator, (ii) an immunosuppressive agent and (iii) an aldosterone antagonist for treating and/or preventing ischemia in an ex vivo organ prior to or during transplantation.

In one embodiment, the present invention relates to use of a combination comprising at least two of the following components: (i) exenatide, or a functional derivative or analogue, or pharmaceutically acceptable salt thereof; (ii) cyclosporine, or a functional derivative or analogue, or pharmaceutically acceptable salt thereof; and (iii) potassium canrenoate, or a functional derivative or analogue thereof for treating and/or preventing ischemia in an ex vivo organ prior to or during transplantation.

An ex vivo (removed from the body) organ can be susceptible to reperfusion injury due to lack of blood flow. Therefore, the combination of the present invention can be used to prevent reperfusion injury in the removed organ. Preferably, the organ is a heart, liver or kidney, more preferably, a heart.

In some embodiments, the removed organ is placed in a standard buffered solution, such as those commonly used in the art, containing the combination of the invention. For example, a removed heart can be placed in a cardioplegic solution containing exenatide and cyclosporine. The concentration of exenatide, cyclosporine and potassium canrenoate useful in the standard buffered solution can be easily determined by those skilled in the art. Such concentrations may be, for example, between about 0.1 nM to about 10 μM, preferably about 1 nM to about 10 μM.

EXAMPLES

The present invention is further illustrated by the following examples, which should not be construed as limiting in any way.

Example 1. Effects of Combined Exenatide and Cyclosporine Treatment in a Rabbit Model of Acute Myocardial Infarction Injury Studies suggest that treatment with exenatide can attenuate/mitigate myocardial injury resulting from an ischemia-reperfusion (I/R) insult as can occur clinically following acute myocardial infarction (AMI) and/or percutaneous coronary intervention/angioplasty (PCI). Exenatide (0.150 μg/Kg IV bolus), when given prior to the onset of reperfusion, may have myocardial sparing effects. In addition, studies suggest that treatment with cyclosporine-A (CsA) can attenuate/mitigate myocardial injury resulting from an I/R insult as can occur clinically following AMI and/or PCI. CsA (2.5 mg/Kg IV bolus), when given prior to the onset of reperfusion, may have myocardial sparing effects. This study was designed to test the combined cardioprotective effects of exenatide and CsA in a setting that mimics the clinical scenario of an acute I/R insult. The study was conducted under the hypothesis that combined treatment with exenatide and CsA after the onset of ischemia (but prior to reperfusion) would provide a more pronounced myocardial protective effect compared to exenatide or cyclosporine treatment alone.

New Zealand White rabbits were used in this study. The rabbits were males, >8 weeks in age and with a weight between 2.9 and 3.8 Kg. Approvals from the Ethical Committees and the veterinary authorities were obtained before the study was started. Environmental controls in the animal rooms were set to maintain temperature of 22° to 28° C. and relative humidity between 30% and 70%. Room temperature and humidity were recorded hourly and monitored daily. There were approximately 10-15 air exchanges per hour in the animal rooms. Photoperiod was 12-hours light and 12-hours dark. Routine daily observations were performed. Certified standard rabbit diet was provided, approximately 180 grams per day from arrival to the facility.

Exenatide peptide [Byetta®, 10 μg/injected dose (40 μl), Eli Lilly Nederland B.V.] and. cyclosporine A [CsA, Sandimmun® (50 mg/ml) Novartis Pharma A.G., Switzerland] are used as the test articles, either in monotherapy or in combined therapy. Dosing solutions of exenatide (0.15 μg/Kg in of normal saline) and/or CsA (2.5 mg/Kg in normal saline) were prepared just before the administration to the rabbits. Normal saline (0.9% NaCl) was used as a control.

The test/control articles were given intravenously, under general anaesthesia, in order to mimic the expected route of administration in the clinical setting of acute myocardial infarction and primary percutaneous coronary intervention. Intravenous boluses were administered via a peripheral vein (rabbit auricular vein).

The study followed a predetermined placebo and sham controlled design. In brief, 80 healthy, acclimatized, male rabbits were randomly assigned to one of three study arms. Arm A (n=4, SHAM) includes sham-operated time-controls treated with normal saline (NS; IV); Arm B (n=18, CONTROL/PLACEBO) includes I/R animals treated with normal saline (NS; IV); Arm C (n=18, EXENATIDE, 0.15 μg/Kg) includes I/R animals treated with exenatide; Arm D (n=18, CYCLOSPORINE, 2.5 mg/Kg, IV) includes I/R animals treated with CsA; Arm E (n=22, EXENATIDE+ CYCLOSPORINE, IV) includes I/R animals treated with exenatide and CsA.

In I/R groups (arm B, C, D and E), rabbits were subjected to 40 min regional ischemia of the heart (coronary occlusion), followed by 120 min (2 h) reperfusion. In all cases, treatments (intravenous bolus administration of NS or exenatide or CsA or exenatide plus CsA) were performed 30 min after the onset of ischemia (10 min before the initiation of reperfusion). In all cases, cardiovascular function was monitored both prior to and during ischemia, as well as for up to 120 min (2 h) post-reperfusion. The experiments were terminated 2 h post-reperfusion (end of study); irreversible myocardial injury (infarct size by histomorphometry) at this time-point was evaluated, and was the primary-end-point of the study. The study design is summarized in Table 1.

TABLE 1

Experimental protocol

| Group | Study Group (no. of animals) | Ischemia Time | Reperfusion Time |
|---|---|---|---|
| A | SHAM - for surgery without ischemia (n = 4) | 0 min (Last 10 min with NS) | 120 min of placebo (NS) |
| B | CONTROL/PLACEBO (n = 18) | 40 min (Last 10 min with NS) | 120 min of placebo (NS) |
| C | EXENATIDE 0.15 µg/Kg (n = 18) | 40 min (Last 10 min with exenatide) | 120 min of exenatide |
| D | CYCLOSPORINE 2.5 mg/Kg (n = 18) | 40 min (Last 10 min with CsA) | 120 min of CsA |
| E | EXENATIDE + CYCLOSPORINE (n = 22) | 40 min (Last 10 min with exenatide + CsA) | 120 min of exenatide + CsA |

Anaesthesia/Surgical Preparation.

General anesthesia was induced intramuscularly (IM) with a ketamine (~35-50 mg/Kg) and xylazine (~5-10 mg/Kg) mixture. In order to preserve autonomic function and to maintain anesthesia throughout the experimental procedure, animals received additional anesthesia as required (~10-15 mg ketamine/30 min or ~15-20 mg/Kg sodium pentobarbital). A venous catheter was placed in a peripheral vein (e.g., ear auricular vein) for the administration of additional anesthetics and normal saline/test articles. The effect of anesthesia is assessed by (i) the total abolishment of animal's corneal reflex, (ii) the total abolishment of animal's respiratory centre and the total mechanical ventilation without any resistance to airflow caused by animal's spontaneous breathing, and (iii) the stability of the hemodynamic parameters. A cuffed tracheal tube was placed via a tracheotomy (ventral midline incision) and used to mechanically ventilate the lungs with a 95% $O_2$/5% $CO_2$ mixture via a volume-cycled animal ventilator (~40 breaths/min with a tidal volume of ~12.5 ml/Kg) in order to sustain $PaCO_2$ values broadly within the physiological range. Throughout the experimental procedure, electrocardiogram, arterial pressure, cardiac pulses, and capnogram were continuously monitored. A temperature probe was inserted into the rectum and body temperature was maintained using a heating pad. Finally, an arterial catheter was placed in a peripheral artery (e.g., ear) for blood sampling.

Subsequently, the animals were placed in left-lateral recumbence and the chest was surgically opened with a left thoracotomy. The chest was opened through the left fourth intercostals space. The beating heart was exposed and the pericardium was incised. Under the atrial appendage, the first large anterolateral branch of the circumflex artery and if necessary, depending on each animal's coronary anatomy, the circumflex artery itself, was circled with a 3-0 silk suture. Coronary artery occlusion in this region normally results in ischemia of a large territory of the anterolateral and apical ventricular wall. The ends of the suture were threaded through a small piece of polyethylene tubing, forming a snare. Ischemia was induced by pulling the thread through the tubing, which was firmly positioned against the coronary arterial wall with the aid of a small clamp. Ischemia resulted in ST elevation on the electrocardiogram and a change in the color (i.e., cyanotic) of the myocardium. After 30 min of ischemia, the animals administered with IV bolus of either vehicle (normal saline) or exenatide or CsA or the combination of exenatide and CsA; ischemia was continued for additional 10 min (i.e., 40 min total ischemia time) after the treatment. At the end of ischemic period, the coronary snares were released and the previous ischemic myocardium was reperfused for up to 2 hours. It should be noted that in sham-operated animals the vessel snares were manipulated at the time of ischemia-reperfusion onset, but were not either tightened or loosened.

Hemodynamic variables and rectal temperature were monitored and recorded at 6 predetermined time-points: post-anesthesia (baseline), just before ischemia initiation (preocclusion), 30 min (vehicle/test articles administration) of ischemia, as well as at 30, 60, and 120 min post reperfusion. In addition, in order to determine/quantify the degree of irreversible myocardial injury (i.e., infarction) resulting from the I/R insult with and without exenatide or CsA or their combination, infarcted area were evaluated.

Blood Samples.

Venous (<3 mL) whole blood samples were collected for the evaluation of myocardial injury via cardiac biomarker analyses at two data-collection time-points: baseline, and 120 min post-reperfusion. Cardiac troponin-I (cTnI), as the most valuable and reliable clinically used biomarker, was measured. cTnI was determined with a biochemical analyzer (Triage® Cardiac Panel, Alere San Diego, Inc. CA, USA).

Histopathology/Histomorphometry.

At the completion of the protocol, irreversible myocardial injury (i.e., infarction) resulting from the I/R insult was evaluated. In brief, after the end of reperfusion, hearts were excised, mounted on an apparatus, and perfused with normal saline for 2 min for blood removal. Then the coronary ligature was retightened at the same site and 5 mL of green fluorescent polymer microsphere solution (8 mg/ml; diameter 3-8 µm; Fluoro-Max™, Thermo Scientific, CA, USA) was infused for the separation of the normally perfused area (no ischemic area) and to delineate the myocardial area-at-risk (AAR, ischemic area) during ischemia. Hearts were kept at −20° C. for 24 hours and sectioned perpendicular to its long axis (from apex to base) into 3 mm thick slices. Subsequently, the slices were incubated for 20 min in 2% triphenyl-tetrazolium-chrolide (TTC, Sigma, St. Louis, Mo., USA) at 37° C., and fixed in a 10% non-buffered formalin solution.

Following fixation, the total left ventricular area (LV), the area-at-risk (AAR), and the infarct area (IF) were delineated/measured digitally. With a wavelength of 366 nm UV light, it was separated in each slide the ischemic area (AAR) from infarcted zone (IF) and no ischemic area. All areas were traced onto an acetate sheet. The tracings were subsequently imported into an image analysis program (Image J; National Institutes of Health), and computer-assisted planometry was performed to determine the overall size of the left ventricular (LV), the area-at-risk (AAR) and the infarct (IF). For each slide, the AAR was expressed as a percentage of the LV area (AAR/LV), and the IF was expressed as a percentage of the AAR (IF/AAR). In all cases, quantitative histomorphometry was performed by personnel blinded to the treatment assignment/study-design.

Data Analysis/Statistics.

Obtained data from the above experiment procedure were tabulated and calculated using Excel work sheets. Statistical analysis was performed with SPSS version 21.0 (SPSS Inc., IL, USA). Values are presented as mean±standard error (SEM). Statistical comparisons of numeric variables among the three groups were analyzed using the one-way analysis of variance (ANOVA) model with Bonferroni correction analysis. A calculated P-value of less than 0.05 was considered to be statistically significant.

Animal Observations/Results.

Hemodynamic variables, mean arterial pressures and heart rate, are shown in the Table 2. Baseline values were similar in all groups. As we typically see in our rabbit model, arterial pressures decrease after surgery and occlusion and most significantly at the end of reperfusion. There were no significant differences among groups in this pressure variable. All groups followed a similar pattern over time.

TABLE 2

Hemodynamic parameters[a]

| Group | Baseline HR MAP | Pre-occlusion HR MAP | 30 min of Ischemia HR MAP | 30 min of Reperfusion HR MAP | 60 min of Reperfusion HR MAP | 120 min of Reperfusion HR MAP |
|---|---|---|---|---|---|---|
| SHAM | 221 ± 5 | 225 ± 7 | 228 ± 7 | 227 ± 5 | 229 ± 4 | 231 ± 3 |
|  | 89 ± 6 | 71 ± 5 | 73 ± 6 | 69 ± 3 | 68 ± 3 | 70 ± 4 |
| CONTROL | 208 ± 6 | 215 ± 7 | 218 ± 7 | 217 ± 5 | 219 ± 6 | 221 ± 8 |
|  | 83 ± 2 | 68 ± 3 | 70 ± 4 | 62 ± 4 | 56 ± 2 | 44 ± 3 |
| EXENATIDE | 217 ± 11 | 220 ± 3 | 219 ± 5 | 221 ± 3 | 224 ± 6 | 226 ± 2 |
|  | 86 ± 3 | 59 ± 4 | 64 ± 4 | 58 ± 3 | 54 ± 2 | 50 ± 3 |
| CYCLOSPORINE | 215 ± 2 | 218 ± 6 | 220 ± 4 | 218 ± 3 | 224 ± 8 | 225 ± 2 |
|  | 81 ± 3 | 70 ± 2 | 67 ± 3 | 66 ± 3 | 57 ± 2 | 47 ± 2 |
| EXENATIDE + CYCLOSPORINE | 219 ± 3 | 223 ± 9 | 224 ± 5 | 221 ± 7 | 226 ± 3 | 228 ± 3 |
|  | 83 ± 2 | 64 ± 2 | 69 ± 4 | 66 ± 2 | 66 ± 2 | 51 ± 3 |

[a]Values are mean ± SEM; HR: mean heart rate in beats/min; MAP: mean arterial blood pressure;

The LV size and AAR size were comparable in all-treated animals, indicating that the initial left ventricular and ischemic area did not differ significantly between the groups. Although the administration of exenatide or CsA resulted in decreased infarct size compared to the control, the administration of the combination of exenatide and CsA resulted in a superior decrease of infarct size. Similarly, whereas exenatide or CsA reduced cTnI release by 48% and 36%, respectively, the combined therapy of exenatide and cyclosporine reduced cTnI release by 61% (62.6±10.7, P<0.001).

Table 3 presents data showing cardiac troponin I levels, the ratios of area of risk to left ventricular, infarcted area to left ventricular, and infarcted area to area of risk for each of group used in this study.

TABLE 3

Study biochemical and histopathology Results

| Group | cTnI (ng/mL) mean ± SEM | AAR/LV (%) mean ± SEM | IF/LV (%) mean ± SEM | IF/AAR (%) mean ± SEM | Different (%) in IF/AAR from Control | Significance in IF/AAR versus Control |
|---|---|---|---|---|---|---|
| SHAM n = 4 | 10.5 ± 3.5 | 56.5 ± 7 | 1.21 ± 0.2 | 2.3 ± 0.4 | −94 | P < 0.001 |
| CONTROL n = 18 | 159 ± 10.4 | 58 ± 2.4 | 21.9 ± 7.8 | 37.7 ± 2.1 |  |  |
| EXENATIDE n = 18 (0.15 µg/Kg) | 82.6 ± 7 | 55.3 ± 2.2 | 12.8 ± 4.9 | 23.5 ± 2 | −38 | P < 0.001 |
| CYCLOSPORINE n = 18 (2.5 mg/Kg) | 101.7 ± 10 | 63.2 ± 2.5 | 14.28 ± 6.5 | 22.7 ± 2.3 | −40 | P < 0.01 |
| EXENATIDE + CYCLOSPORINE n = 22 | 62.6 ± 10.7 | 61.5 ± 3.4 | 10.09 ± 5.1 | 16.8 ± 1.7 | −55 | P < 0.001 |

These results show that in a standardized rabbit model of acute myocardial ischemia and reperfusion injury, the combined therapy of exenatide and CsA when administrated as an IV bolus (0.15 µg/Kg and 2.5 mg/Kg, respectively) at 10 min before the initiation of reperfusion was able to produce a greater reduction in the myocardial infarct size compared to exenatide or CsA monotherapy groups. Accordingly, these results demonstrate for first time that in therapy of myocardial reperfusion injury the combined administration of cyclosporine and exenatide is more beneficial and advantageous and provides superior clinical outcome against therapies either with cyclosporine or exenatide alone. As such, combined exenatide and CsA is exceptionally useful in methods at preventing and treating ischemia-reperfusion injury in mammalian subjects.

Example 2. Dose-Dependent Effects of Combined Exenatide and Cyclosporine Treatment in a Rat Model of Acute Myocardial Infarction Injury This study was designed to investigate the cardioprotective effects of exenatide, CsA and their combinations in a variety of doses and in a rat model of myocardial reperfusion injury. The study was conducted under the hypothesis that combination therapy with exenatide and CsA, after the onset of ischemia and prior to reperfusion, would also result in enhanced reduction of infarct size in an additional animal model.

Wistar rats were used in this study. The rats were males and with a weight between 266 and 370 g. Approvals from the Ethical Committees and the veterinary authorities were obtained before the study was started. The animals were housed in individually ventilated cages using HEPA-filtered air, which conform to the size recommendations in the most recent Guide for the Care and Use of Laboratory Animals DHEW (NIH) and Directive 2010/63/EU on the protection of animals used for scientific purposes. Environmental controls in the animal rooms were set to maintain temperature of 22° to 28° C. and relative humidity between 30% and 70%. Litter material placed beneath the cage was changed at least three times a week. There were approximately 10-15 air exchanges per hour in the animal rooms. Photoperiod was 12-hours light and 12-hours dark. Routine daily observations were performed. The animals were conditioned to the housing facilities for at least 3 days prior to testing. Standard laboratory rat chow and filtered tap water was available ad libitum.

Exenatide (Byetta®, Eli Lilly Nederland B.V.) and CsA (Sandimmun®, Novartis Pharma A.G., Switzerland) are used as the test articles, either in monotherapy or in combined therapy. Dosing solutions of exenatide and/or CsA were prepared just before the administration to the rats. Normal saline (0.9% NaCl) was used as a control.

The study followed a predetermined placebo controlled design. In brief, 130 healthy, acclimatized, male rats were randomly assigned to one of ten study arms. All animals were subjected to 30 min regional ischemia of the heart (coronary occlusion), followed by 120 min (2 h) reperfusion. In all cases, treatments (intravenous bolus administration of NS or exenatide or CsA or their combinations) were performed 20 min after the onset of ischemia (10 min before the initiation of reperfusion). In all cases, cardiovascular function was monitored both prior to and during ischemia, as well as for up to 120 min (2 h) post-reperfusion. The experiments were terminated 2 h post-reperfusion (end of study); irreversible myocardial injury (infarct size by histomorphometry) at this time-point was evaluated, and was the primary-end-point of the study. The study design is summarized in Table 4.

TABLE 4

Experimental protocol

| Study Group (no. of animals) | Ischemia Time | Reperfusion Time |
|---|---|---|
| CONTROL (saline) (n = 11) | 30 min (Last 10 min with saline) | 120 min of saline |
| EXENATIDE 0.03 µg/Kg (n = 11) | 30 min (Last 10 min with exenatide) | 120 min of exenatide |
| CYCLOSPORINE 0.5 mg/Kg (n = 12) | 30 min (Last 10 min with CsA) | 120 min of CsA |
| EXENATIDE 0.03 µg/Kg + CYCLOSPORINE 0.5 mg/Kg (n = 12) | 30 min (Last 10 min with exenatide and CsA) | 120 min of exenatide and CsA |
| EXENATIDE 0.15 µg/Kg (n = 12) | 30 min (Last 10 min with exenatide) | 120 min of exenatide |
| CYCLOSPORINE 2.5 mg/Kg (n = 12) | 30 min (Last 10 min with CsA) | 120 min of CsA |
| EXENATIDE 0.15 µg/Kg + CYCLOSPORINE 2.5 mg/Kg (n = 11) | 30 min (Last 10 min with exenatide and CsA) | 120 min of exenatide and CsA |
| EXENATIDE 1 µg/Kg (n = 12) | 30 min (Last 10 min with exenatide) | 120 min of exenatide |
| CYCLOSPORINE 10 mg/Kg (n = 14) | 30 min (Last 10 min with CsA) | 120 min of CsA |
| EXENATIDE 1 µg/Kg + CYCLOSPORINE 10 mg/Kg (n = 11) | 30 min (Last 10 min with exenatide and CsA) | 120 min of exenatide and CsA |

Anaesthesia/Surgical Preparation.

Male Wistar rats were anaesthetized by intraperitoneal (IP) injection of pentobarbital (Euthazol, Produlab Pharma b.v., Raamsdonksveer, The Netherlands; 60 mg/Kg bolus dose followed by 15-20 mg/Kg when required during the experiment). The rats were weighted and stomach and chest areas shaved. Maintenance of the body temperature was assisted using a constant temperature heating pad. The trachea was intubated with a plastic cannula connected to a rodent ventilator. The animals were ventilated with room air (6.2 ml/Kg, 70±5 breath/min). Blood pressure, surface-lead ECG, and body core temperature were monitored throughout the experiments to ensure the stability of the preparation. The right carotid artery was cannulated for measurement of blood pressure and the right jugular vein was cannulated for the administration of the test articles. A thoracotomy was performed at the $5^{th}$ intercostals space and the heart was exposed. A 5-0 Prolene suture was placed around the left descending coronary artery. The coronary artery was then occluded for 30 min by placing the ligature through a small piece of plastic tubing and pulling the snare tightly in place using a haemostat. After 30 min of coronary occlusion, reperfusion was initiated by releasing the snare and continued for 120 min.

Hemodynamic variables were monitored and recorded at 6 predetermined time-points: post-anesthesia (baseline), just before ischemia initiation (preocclusion), 20 min (vehicle/test articles administration) of ischemia, as well as at 30, 60, and 120 min post reperfusion. In addition, in order to determine/quantify the degree of irreversible myocardial injury (i.e., infarction) resulting from the I/R insult with and without exenatide or CsA or the exenatide and Csa treatment, cardiac biomarkers as well as infarct area were evaluated.

Histopathology/Histomorphometry.

At the end of the 120 min reperfusion period, the heart was taken out and infarct size was determined. Briefly, the left anterior descending coronary artery was re-occluded and the heart was perfused with 4 ml of 0.3% (w/v) Evans-blue dye (Sigma-Aldrich) with a constant 100cmH$_2$O pressure into the aorta to delineate the area-at-risk zone. The non-ischemic perfused tissue area was stained blue, while the risk zone remained unstained. Stained hearts were rapidly frozen (−20° C. for at least 2 hours), cut into 2 mm thick slices and each slice was incubated at 37° C. in 1.5 ml of 1% (w/v) TTC (Merck Biosciences) dissolved in 50 mM phosphate buffer (pH 7.4) for 10 min. Slices were then transferred to 10% formalin solution for 5 min.

Following fixation, the total left ventricular area (LV), the area-at-risk (AAR), and the infarct area (IF) were delineated/measured digitally. Slices were placed between glass plates and digital photos were taken from both sides of the heart slices. The differently stained areas of images were quantified by digital planimetry (Infarctsize™ 2.5, Pharmahungary, Szeged, Hungary). Evaluation of all images was carried out in a blinded manner by an experienced person throughout the study. For each slide, the AAR was expressed as a percentage of the LV area (AAR/LV), and the IF was expressed as a percentage of the AAR (IF/AAR).

Data Analysis/Statistics.

Obtained data from the above experiment procedure were tabulated and calculated using Excel work sheets. Statistical analysis was performed with SPSS version 21.0 (SPSS Inc., IL, USA). Values are presented as mean±standard error (SEM). Differences among means of endpoint measurements (i.e. infarct size, AAR) were analyzed by using one-way-ANOVA followed by Tukey post hoc test to make comparisons of each group to the control when appropriate. Differences among means of continuous variables (i.e. hemodynamic data) were analyzed by repeated measures two-way-ANOVA followed by Tukey posthoc test. A calculated P-value of less than 0.05 was considered to be statistically significant.

Animal Observations/Results.

Hemodynamic variables, mean arterial pressures and heart rate, are shown in the Table 5. Baseline values were similar in all groups. As we typically see in our rat model, arterial pressures decrease after surgery and occlusion and most significantly at the end of reperfusion. There were no significant differences among groups in this pressure variable. All groups followed a similar pattern over time.

TABLE 5

Hemodynamic parameters

| Group | Baseline HR MAP | Pre-occlusion HR MAP | 20 min of Ischemia HR MAP | 30 min of Reperfusion HR MAP | 60 min of Reperfusion HR MAP | 120 min of Reperfusion HR MAP |
|---|---|---|---|---|---|---|
| CONTROL (saline) (n = 11) | 427 112 | 455 114 | 434 102 | 434 88 | 421 82 | 441 87 |
| EXENATIDE 0.03 µg/Kg (n = 11) | 449 108 | 439 93 | 404 71 | 426 69 | 404 72 | 388 71 |
| CYCLOSPORINE 0.5 mg/Kg (n = 12) | 421 115 | 444 110 | 419 89 | 419 95 | 421 80 | 412 72 |
| EXENATIDE 0.03 µg/Kg + CYCLOSPORINE 0.5 mg/Kg (n = 12) | 430 111 | 444 95 | 413 65 | 410 73 | 402 72 | 416 67 |
| EXENATIDE 0.15 µg/Kg (n = 12) | 426 119 | 455 107 | 439 88 | 407 75 | 435 82 | 435 77 |
| CYCLOSPORINE 2.5 mg/Kg (n = 12) | 425 109 | 468 92 | 411 72 | 408 81 | 438 84 | 374 67 |
| EXENATIDE 0.15 µg/Kg + CYCLOSPORINE 2.5 mg/Kg (n = 11) | 432 109 | 460 109 | 415 81 | 438 87 | 388 81 | 404 68 |
| EXENATIDE 1 µg/Kg (n = 12) | 418 111 | 449 111 | 439 92 | 455 93 | 469 94 | 404 86 |
| CYCLOSPORINE 10 mg/Kg (n = 14) | 424 114 | 445 105 | 411 93 | 400 89 | 425 90 | 404 86 |
| EXENATIDE 1 µg/Kg + CYCLOSPORINE 10 mg/Kg (n = 11) | 425 115 | 447 107 | 441 85 | 439 89 | 454 90 | 469 87 |

HR: mean heart rate in beats/min;
MAP: mean arterial blood pressure in mmHg . . .

The LV size and AAR size were comparable in all-treated animals, indicating that the initial left ventricular and ischemic areas did not differ significantly between the groups. Administration of exenatide or CsA exhibited a dose-dependent effect. In particular, treatment of animals with lower doses of exenatide and CsA resulted in significant decreased infarct size compared to the control, whereas higher doses were without effects. Interestingly, the administration of the combination of low doses of exenatide and CsA resulted in a superior decrease of infarct size. Whereas, exenatide at dose of 0.03 μg/Kg reduced infarcted area by 27% (45.9±1.4; P<0.05) and CsA at 0.5 mg/Kg by 26.6% (46.2±3.7; P<0.05), respectively, the combined therapy of exenatide and CsA reduced infarcted area by 39.1% (38.3±2.7; P<0.05), as compared to control (62.9±3.7).

Table 6 presents data showing the ratios of area of risk to left ventricular, and infarcted area to area of risk for each of group of the study.

or exenatide alone. As such, combined exenatide and CsA is exceptionally useful in methods at preventing and treating ischemia-reperfusion injury in mammalian subjects.

Example 3. Effects of Combined Exenatide and Potassium Canrenoate Treatment in a Rabbit Model of Acute Myocardial Infarction Injury Studies suggest that treatment with potassium canrenoate can attenuate/mitigate myocardial injury resulting from an I/R insult as can occur clinically following AMI and/or PCI. This study was designed to test the combined cardioprotective effects of exenatide and potassium canrenoate in a setting that mimics the clinical scenario of an acute I/R insult. The study was conducted under the hypothesis that combined treatment with exenatide and potassium canrenoate after the onset of ischemia (but prior to reperfusion)

TABLE 6

Study histopathology results

| Group | AAR/LV (% mean ± SEM) | IF/AAR (% mean ± SEM) | Different (%) in IF/AAR from Control | Significance in IF/AAR versus Control |
|---|---|---|---|---|
| CONTROL (saline) (n = 11) | 47.7 ± 2.9 | 62.9 ± 3.7 | — | |
| EXENATIDE 0.03 μg/Kg (n = 11) | 44.1 ± 3 | 45.9 ± 1.4 | −27 | P < 0.05 |
| CYCLOSPORINE 0.5 mg/Kg (n = 12) | 42.6 ± 2.2 | 46.2 ± 3.7 | −26.6 | P < 0.05 |
| EXENATIDE 0.03 μg/Kg + CYCLOSPORINE 0.5 mg/Kg (n = 12) | 42.1 ± 3.5 | 38.3 ± 2.7 | −39.1 | P < 0.05 |
| EXENATIDE 0.15 μg/Kg (n = 12) | 49.8 ± 3.5 | 61.5 ± 4.1 | −2.2 | Non significant |
| CYCLOSPORINE 2.5 mg/Kg (n = 12) | 47.3 ± 2.6 | 61 ± 4.1 | −3 | Non significant |
| EXENATIDE 0.15 μg/Kg + CYCLOSPORINE 2.5 mg/Kg (n = 11) | 44.7 ± 3.5 | 58.8 ± 5.1 | −6.5 | Non significant |
| EXENATIDE 1 μg/Kg (n = 12) | 38.9 ± 2.4 | 52.6 ± 2.9 | 16.4 | Non significant |
| CYCLOSPORINE 10 mg/Kg (n = 14) | 38.7 ± 3.1 | 54.3 ± 3.5 | −13.7 | Non significant |
| EXENATIDE 1 μg/Kg + CYCLOSPORINE 10 mg/Kg (n = 11) | 46.2 ± 4.1 | 51.5 ± 2.5 | −18.1 | Non significant |

These results show that in an additional standardized animal (rat) model of acute myocardial ischemia and reperfusion injury, the combined therapy of exenatide and CsA was also able to produce a greater reduction in the myocardial infarct size compared to exenatide or CsA monotherapies. However, in the present rat model the cardioprotective effect was evident in lower doses compared to rabbit model of Example 1, indicating that different species may respond differently to exenatide or CsA or to their combination. The fact that the duration of the ischemia was longer in the rabbit model may also be accountable for the difference of the effects seen in the two species. Nevertheless, these results again demonstrate that in therapy of myocardial reperfusion injury the combined administration of CsA and exenatide is more beneficial and advantageous and provides superior clinical outcome against therapies either with cyclosporine would provide a more pronounced myocardial protective effect compared to exenatide or potassium canrenoate treatment alone.

New Zealand White rabbits were used in this study. The rabbits were males, >8 week in age and with a weight between 2.6 and 3.8 Kg. All animals were treated according to the Directive 2010/63/UE European Convention for the Protection of Vertebrate Animals used for Experimental and other Scientific Purposes, and conformed to the Guide for the Care and Use of Laboratory Animals published by the US National Institutes of Health (NIH Publication No. 85-23, revised 1985). Approvals from the Ethical Committees and the veterinary authorities were obtained before the study was started. Environmental controls in the animal rooms were set to maintain temperature of 22° to 28° C. and relative humidity between 30% and 70%. Room temperature and humidity were recorded hourly and monitored daily. There were approximately 10-15 air exchanges per hour in the animal rooms. Photoperiod was 12-hours light and 12-hours dark. Routine daily observations were performed. Certified standard rabbit diet was provided, approximately 180 grams per day from arrival to the facility.

Exenatide (Byetta®; Eli Lilly Nederland B.V.] and potassium canrenoate (Sigma-Aldrich, Germany) are used as the test articles, either in monotherapy or in combined therapy. Dosing solutions of exenatide (0.15 µg/Kg in of normal saline) and/or potassium canrenoate (1 mg/Kg in normal saline) were prepared just before the administration to the rabbits. Normal saline (0.9% NaCl) was used as a control.

The test/control articles were given intravenously, under general anaesthesia, in order to mimic the expected route of administration in the clinical setting of acute myocardial infarction and primary percutaneous coronary intervention. Intravenous boluses were administered via a peripheral vein (rabbit auricular vein).

The study followed a predetermined placebo controlled design. In brief, 52 healthy, acclimatized, male rabbits were randomly assigned to one of four study arms. In all groups, rabbits were subjected to 30 min regional ischemia of the heart (coronary occlusion), followed by 180 min (3 h) reperfusion. In all cases, treatments (intravenous bolus administration of saline or exenatide or potassium canrenoate or their combination) were performed 15 min after the onset of ischemia (15 min before the initiation of reperfusion). The experiments were terminated 3 h post-reperfusion (end of study); irreversible myocardial injury (infarct size by histomorphometry) at this time-point was evaluated, and was the primary-end-point of the study. The study design is summarized in Table 7.

TABLE 7

Experimental protocol

| Study Group (no. of animals) | Ischemia Time | Reperfusion Time |
| --- | --- | --- |
| CONTROL (n = 12) | 30 min (Last 15 min with saline) | 180 min of placebo (saline) |
| EXENATIDE 0.15 µg/Kg (n = 11) | 30 min (Last 15 min with exenatide) | 180 min of exenatide |
| P. CANRENOATE 1 mg/Kg (n = 12) | 30 min (Last 15 min with potassium canrenoate) | 180 min of potassium canrenoate |
| EXENATIDE + P. CANRENOATE (n = 17) | 30 min (Last 15 min with exenatide and potassium canrenoate) | 180 min of exenatide and potassium canrenoate |

Anaesthesia/Surgical Preparation.

General anesthesia was induced intramuscularly (IM) with a ketamine (~35-50 mg/Kg) and xylazine (~5-10 mg/Kg) mixture. In order to preserve autonomic function and to maintain anesthesia throughout the experimental procedure, animals received additional anesthesia as required (~10-15 mg ketamine/30 min or ~15-20 mg/Kg sodium pentobarbital). A venous catheter was placed in a peripheral vein (e.g., ear auricular vein) for the administration of additional anesthetics and normal saline/test articles. A cuffed tracheal tube was placed via a tracheotomy (ventral midline incision) and used to mechanically ventilate the lungs with a 95% $O_2$/5% $CO_2$ mixture via a volume-cycled animal ventilator (~40 breaths/min with a tidal volume of ~12.5 ml/Kg) in order to sustain $PaCO_2$ values broadly within the physiological range.

Subsequently, the animals were placed in left-lateral recumbence and the chest was surgically opened with a left thoracotomy. The chest was opened through the left fourth intercostals space. The beating heart was exposed and the pericardium was incised. Under the atrial appendage, the left anterior descending coronary artery (LAD) was circled with a 3-0 silk suture. Coronary artery occlusion in this region normally results in ischemia of a large territory of the anterolateral and apical ventricular wall. The ends of the suture were threaded through a small piece of polyethylene tubing, forming a snare. Ischemia was induced by pulling the thread through the tubing, which was firmly positioned against the coronary arterial wall with the aid of a small clamp. Ischemia resulted in a change in the color (i.e., cyanotic) of the myocardium. After 15 min of ischemia, the animals administered with IV bolus of either vehicle (normal saline) or indicated test article; ischemia was continued for additional 15 min (i.e., 30 min total ischemia time) after the treatment. At the end of ischemic period, the coronary snares were released and the previous ischemic myocardium was reperfused for up to 3 hours. In order to determine/quantify the degree of irreversible myocardial injury (i.e., infarction) resulting from the ischemia and reperfusion insult with and without indicated treatment, infarct area were evaluated.

Histopathology/Histomorphometry.

At the completion of the protocol, irreversible myocardial injury (i.e., infarction) resulting from the I/R insult was evaluated. In brief, after the end of reperfusion, hearts were excised, mounted on an apparatus, and perfused with normal saline for 2 min for blood removal. Then the coronary ligature was retightened at the same site and 5 mL of green fluorescent polymer microsphere solution (8 mg/ml; diameter 3-8 µm; Fluoro-Max™, Thermo Scientific, CA, USA) was infused for the separation of the normally perfused area (no ischemic area) and to delineate the myocardial area-at-risk (AAR, ischemic area) during ischemia. Hearts were kept at −20° C. for 24 hours and sectioned perpendicular to its long axis (from apex to base) into 3 mm thick slices. Subsequently, the slices were incubated for 20 min in 2% (TTC, Sigma) at 37° C., and fixed in a 10% non-buffered formalin solution.

Following fixation, the total left ventricular area (LV), the area-at-risk (AAR), and the infarct area (IF) were delineated/measured digitally. With a wavelength of 366 nm UV light, it was separated in each slide the ischemic area (AAR) from infarcted zone (IF) and no ischemic area. All areas were traced onto an acetate sheet. The tracings were subsequently imported into an image analysis program (Image J; National Institutes of Health), and computer-assisted planimetry was performed to determine the overall size of the left ventricular (LV), the area-at-risk (AAR) and the infarct (IF). For each slide, the AAR was expressed as a percentage of the LV area (AAR/LV), and the IF was expressed as a percentage of the AAR (IF/AAR). In all cases, quantitative histomorphometry was performed by personnel blinded to the treatment assignment/study-design.

Data Analysis/Statistics.

Statistical analysis was performed with SPSS version 21.0 (SPSS Inc., IL, USA). Values are presented as mean±error (SEM). Statistical comparisons of numeric variables among the three groups were analyzed using the one-way ANOVA model with Bonferroni correction analysis. A calculated P-value of less than 0.05 was considered to be statistically significant.

Animal Observations/Results.

The area of the left ventricle (LV) and the ischemic area (AAR) were similar in all animals and did not differ statistically between the study groups. The induction of ischemia (30 min) and reperfusion (180 min) in the control group resulted in significant injury to the myocardium of experimental animals (49.47±3.97%), indicating the sufficient implementation of the model and the reproducibility of the experimental procedure of the study. The exenatide monotherapy (0.150 μg/Kg) caused a reduction of the extent of infarct by 36.2% (31.55±3.31%; P<0.05) compared with the control group. Administration of potassium canrenoate monotherapy (1 mg/Kg) reduced the area of the infarct by 30.5% (34.36±2.83%; P<0.05) compared with the control group. Treatment of combination of exenatide and potassium canrenoate caused a dramatic reduction in the extent of infarct by 73.1% (13.31±2.14%; P<0.001) compared to the control group. Interestingly, the effect of the combination was also statistically significant (P<0.01) compared to the respective exenatide and potassium canrenoate monotherapies.

Table 8 presents data showing the ratios of area of risk to left ventricular and infarcted area to area of risk for each of group used in this study.

TABLE 8

Study histopathology results

| Group | AAR/LV (% mean ± SEM) | IF/AAR (% mean ± SEM) | Different (%) in IF/AAR from Control | Significance in IF/AAR versus Control | Significance in IF/AAR versus monotherapies |
|---|---|---|---|---|---|
| CONTROL (n = 12) | 55.46 ± 2.84 | 49.47 ± 3.97 | — | — | — |
| EXENATIDE 0.15 μg/Kg (n = 11) | 55.01 ± 2.42 | 31.55 ± 3.31 | −36.2 | P < 0.05 | — |
| P. CANRENOATE 1 mg/Kg (n = 12) | 57.67 ± 1.73 | 34.36 ± 2.83 | −30.5 | P < 0.05 | — |
| EXENATIDE + P. CANRENOATE (n = 17) | 56.74 ± 3.46 | 13.31 ± 2.14 | −73.1 | P < 0.001 | P < 0.01 |

These results show that in a standardized rabbit model of acute myocardial ischemia and reperfusion injury, the combined therapy of exenatide and potassium canrenoate when administrated as an IV bolus (0.15 μg/Kg and 1 mg/Kg, respectively) at 15 min before the initiation of reperfusion was able to produce a significantly greater reduction in the myocardial infarct size compared to exenatide or potassium canrenoate monotherapy groups. Furthermore, it is of great interest that the present results provide for first time strong evidence that the combination therapy of potassium canrenoate with exenatide reduced the extent of myocardial injury also in a synergistic manner, since the obtained combination reduction exceeds the sum of the respective monotherapies' reductions. Accordingly, these results demonstrate for first time that in therapy of myocardial reperfusion injury the combined administration of potassium canrenoate and exenatide is more beneficial and advantageous and provides superior clinical outcome against therapies either with potassium canrenoate or exenatide alone. As such, combined exenatide and potassium canrenoate is exceptionally useful in methods at preventing and treating ischemia-reperfusion injury in mammalian subjects.

Example 4. Triple Combination Therapy: Effects of Combined Exenatide, Cyclosporine and Potassium Canrenoate Treatment in a Rabbit Model of Acute Myocardial Infarction Injury This study was designed to test the combined cardioprotective effects of exenatide, cyclosporine (CsA) and potassium canrenoate in a setting that mimics the clinical scenario of an acute I/R insult. The study was conducted under the hypothesis that triple combined treatment with exenatide, CsA and potassium canrenoate after the onset of ischemia (but prior to reperfusion) would provide a more pronounced myocardial protective effect compared to double treatment with exenatide and cyclosporine.

New Zealand White rabbits were used in this study. The rabbits were males, >8 week in age and with a weight between 2.6 and 3.8 Kg. All animals were treated according to the Directive 2010/63/UE European Convention for the Protection of Vertebrate Animals used for Experimental and other Scientific Purposes, and conformed to the Guide for the Care and Use of Laboratory Animals published by the US National Institutes of Health (NIH Publication No. 85-23, revised 1985). Approvals from the Ethical Committees and the veterinary authorities were obtained before the study was started. Environmental controls in the animal rooms were set to maintain temperature of 22° to 28° C. and relative humidity between 30% and 70%. Room temperature and humidity were recorded hourly and monitored daily. There were approximately 10-15 air exchanges per hour in the animal rooms. Photoperiod was 12-hours light and 12-hours dark. Routine daily observations were performed. Certified standard rabbit diet was provided, approximately 180 grams per day from arrival to the facility.

Exenatide (Byetta®; Eli Lilly Nederland B.V.], CsA (Sandimmun®, Novartis Pharma A.G., Switzerland) and potassium canrenoate (Sigma-Aldrich, Germany) are used as the test articles, either in double or in triple combined therapy. Dosing solutions of exenatide, CsA and potassium canrenoate were prepared just before the administration to the rabbits. Normal saline (0.9% NaCl) was used as a control.

The test/control articles were given intravenously, under general anaesthesia, in order to mimic the expected route of administration in the clinical setting of acute myocardial infarction and primary percutaneous coronary intervention. Intravenous boluses were administered via a peripheral vein (rabbit auricular vein).

The study followed a predetermined placebo controlled design. In brief, 55 healthy, acclimatized, male rabbits were randomly assigned to one of four study arms. In all groups, rabbits were subjected to 30 min regional ischemia of the heart (coronary occlusion), followed by 180 min (3 h) reperfusion. In all cases, treatments (intravenous bolus administration of saline or test articles combination) were performed 15 min after the onset of ischemia (15 min before the initiation of reperfusion). The experiments were terminated 3 h post-reperfusion (end of study); irreversible myocardial injury (infarct size by histomorphometry) at this time-point was evaluated, and was the primary-end-point of the study. The study design is summarized in Table 9.

TABLE 9

Experimental protocol

| Study Group (no. of animals) | Ischemia Time | Reperfusion Time |
| --- | --- | --- |
| CONTROL (n = 12) | 30 min (Last 15 min with placebo saline) | 180 min of placebo (saline) |
| EXENATIDE 0.15 μg/Kg + CYCLOSPORINE 0.5 mg/Kg (n = 8) | 30 min (Last 15 min with exenatide and cyclosporine) | 180 min of exenatide and cyclosporine |
| EXENATIDE 0.15 μg/Kg + CYCLOSPORINE 0.5 mg/Kg + P. CANRENOATE 1 mg/Kg (n = 10) | 30 min (Last 15 min with exenatide and cyclosporine and potassium canrenoate) | 180 min of exenatide and cyclosporine and potassium canrenoate |
| EXENATIDE 0.15 μg/Kg + CYCLOSPORINE 1 mg/Kg + P. CANRENOATE 1 mg/Kg (n = 9) | 30 min (Last 15 min with exenatide and cyclosporine and potassium canrenoate) | 180 min of exenatide and cyclosporine and potassium canrenoate |
| EXENATIDE 0.15 μg/Kg + CYCLOSPORINE 2.5 mg/Kg + P. CANRENOATE 1 mg/Kg (n = 16) | 30 min (Last 15 min with exenatide and cyclosporine and potassium canrenoate) | 180 min of exenatide and cyclosporine and potassium canrenoate |

Anaesthesia/Surgical Preparation.

General anesthesia was induced intramuscularly (IM) with a ketamine (~35-50 mg/Kg) and xylazine (~5-10 mg/Kg) mixture. In order to preserve autonomic function and to maintain anesthesia throughout the experimental procedure, animals received additional anesthesia as required (~10-15 mg ketamine/30 min or ~15-20 mg/Kg sodium pentobarbital). A venous catheter was placed in a peripheral vein (e.g., ear auricular vein) for the administration of additional anesthetics and normal saline/test articles. A cuffed tracheal tube was placed via a tracheotomy (ventral midline incision) and used to mechanically ventilate the lungs with a 95% $O_2$/5% $CO_2$ mixture via a volume-cycled animal ventilator (~40 breaths/min with a tidal volume of ~12.5 ml/Kg) in order to sustain $PaCO_2$ values broadly within the physiological range.

Subsequently, the animals were placed in left-lateral recumbence and the chest was surgically opened with a left thoracotomy. The chest was opened through the left fourth intercostals space. The beating heart was exposed and the pericardium was incised. Under the atrial appendage, the left anterior descending coronary artery (LAD) was circled with a 3-0 silk suture. Coronary artery occlusion in this region normally results in ischemia of a large territory of the anterolateral and apical ventricular wall. The ends of the suture were threaded through a small piece of polyethylene tubing, forming a snare. Ischemia was induced by pulling the thread through the tubing, which was firmly positioned against the coronary arterial wall with the aid of a small clamp. Ischemia resulted in a change in the color (i.e., cyanotic) of the myocardium. After 15 min of ischemia, the animals administered with IV bolus of either vehicle (normal saline) or indicated test article; ischemia was continued for additional 15 min (i.e., 30 min total ischemia time) after the treatment. At the end of ischemic period, the coronary snares were released and the previous ischemic myocardium was reperfused for up to 3 hours. In order to determine/quantify the degree of irreversible myocardial injury (i.e., infarction) resulting from the ischemia and reperfusion insult with and without indicated treatment, infarct area was evaluated.

Histopathology/Histomorphometry.

At the completion of the protocol, irreversible myocardial injury (i.e., infarction) resulting from the I/R insult was evaluated. In brief, after the end of reperfusion, hearts were excised, mounted on an apparatus, and perfused with normal saline for 2 min for blood removal. Then the coronary ligature was retightened at the same site and 5 mL of green fluorescent polymer microsphere solution (8 mg/ml; diameter 3-8 μm; Fluoro-Max™, Thermo Scientific, CA, USA) was infused for the separation of the normally perfused area (no ischemic area) and to delineate the myocardial area-at-risk (AAR, ischemic area) during ischemia. Hearts were kept at −20° C. for 24 hours and sectioned perpendicular to its long axis (from apex to base) into 3 mm thick slices. Subsequently, the slices were incubated for 20 min in 2% (TTC, Sigma) at 37° C., and fixed in a 10% non-buffered formalin solution.

Following fixation, the total left ventricular area (LV), the area-at-risk (AAR), and the infarct area (IF) were delineated/measured digitally. With a wavelength of 366 nm UV light, it was separated in each slide the ischemic area (AAR) from infarcted zone (IF) and no ischemic area. All areas were traced onto an acetate sheet. The tracings were subsequently imported into an image analysis program (Image J; National Institutes of Health), and computer-assisted planimetry was performed to determine the overall size of the left ventricular (LV), the area-at-risk (AAR) and the infarct (IF). For each slide, the AAR was expressed as a percentage of the LV area (AAR/LV), and the IF was expressed as a percentage of the AAR (IF/AAR). In all cases, quantitative histomorphometry was performed by personnel blinded to the treatment assignment/study-design.

Data Analysis/Statistics.

Statistical analysis was performed with SPSS version 21.0 (SPSS Inc., IL, USA). Values are presented as mean±error (SEM). Statistical comparisons of numeric variables among the three groups were analyzed using the one-way ANOVA model followed by Fisher LSD post hoc test. A calculated P-value of less than 0.05 was considered to be statistically significant.

Animal Observations/Results.

The area of the left ventricle (LV) and the ischemic area (AAR) were similar in all animals and did not differ statistically between the study groups. Treatment of double combination of exenatide and CsA (0.150 mg/Kg and 0.5 mg/Kg, respectively) caused a reduction of the area of infarction by 50% (24.74±3.8%; P<0.05) compared with the control group (49.47±4). The addition to this treatment of potassium canrenoate (1 mg/Kg) resulted in a further reduction of the area of the infarct by 70.6% (14.56±3%; P<0.001) compared to the control group. Similarly, the administration of a triple combinations of exenatide, potassium canrenoate and CsA 1 mg/Kg reduced the area of the infarct by 74.8% (12.49±2.2%; P<0.001), compared to the control group. Interestingly, the effect of these triple combinations was statistically significant (P<0.05) compared with double combination of exenatide and CsA. However, the administration of a triple combination of exenatide, potassium canrenoate and CsA 2.5 mg/Kg caused a reduction of the extent of infarct by 46.5% (26.48±2.93%; P<0.05), which was not statistically significant compared to double combination of exenatide and CsA.

Table 10 presents data showing the ratios of area of risk to left ventricular and infarcted area to area of risk for each of group used in this study.

Example 5. Effects of Exenatide, Cyclosporine and Potassium Canrenoate and their Double or Triple Combined Therapies in a Mouse Model of Acute Myocardial Infarction Injury This study was designed to test the following:

i) The dose-dependent effects of exenatide, CsA and potassium canrenoate as monotherapy in an additional animal (murine) model of myocardial reperfusion injury.

ii) The effects of exenatide, CsA and potassium canrenoate double combination therapies at doses that are lower than the optimal monotherapy doses.

iii) The effect of exenatide, CsA and potassium canrenoate triple combination therapy at the same dose of each component used in the double combination.

TABLE 10

Study histopathology results

| Group | AAR/LV (% mean ± SEM) | IF/AAR (% mean ± SEM) | Different (%) in IF/AAR from Control | Significance in IF/AAR versus Control | Significance in IF/AAR versus double combination |
|---|---|---|---|---|---|
| CONTROL (n = 12) | 55.46 ± 2.8 | 49.47 ± 4 | — | — | — |
| EXENATIDE 0.15 µg/Kg + CYCLOSPORINE 0.5 mg/Kg (n = 8) | 61.11 ± 5.6 | 24.74 ± 3.8 | −50 | P < 0.05 | — |
| EXENATIDE 0.15 µg/Kg + CYCLOSPORINE 0.5 mg/Kg + P. CANRENOATE 1 mg/Kg (n = 10) | 60.52 ± 4.4 | 14.56 ± 3 | −70.6 | P < 0.001 | P < 0.05 |
| EXENATIDE 0.15 µg/Kg + CYCLOSPORINE 1 mg/Kg + P. CANRENOATE 1 mg/Kg (n = 9) | 54.5 ± 3.7 | 12.49 ± 2.2 | −74.8 | P < 0.001 | P < 0.05 |
| EXENATIDE 0.15 µg/Kg + CYCLOSPORINE 2.5 mg/Kg + P. CANRENOATE 1 mg/Kg (n = 16) | 53.8 ± 2.6 | 26.48 ± 2.9 | −46.5 | P < 0.05 | Non significant |

These results show that in a standardized rabbit model of acute myocardial ischemia and reperfusion injury, the combined administration of exenatide and CsA provides beneficial effect, while the addition of potassium canrenoate to the treatment demonstrated a significant further potentiation of the cardioprotection of the combination. It is of great interest that the present Example provides for first time strong evidence that triple combination therapy of exenatide, CsA and potassium canrenoate produced a greater reduction in the extent of myocardial injury compared to exenatide and CsA combined treatment. Accordingly, these results demonstrate for first time that in therapy of myocardial reperfusion injury the triple combined administration of exenatide, CsA and potassium canrenoate is more beneficial and advantageous and provides superior clinical outcome against either monotherapies or CsA and exenatide administered as combined therapies. As such, combined exenatide, CsA (at least in low doses) and potassium canrenoate is exceptionally useful in methods at preventing and treating ischemia-reperfusion injury in mammalian subjects.

The study was conducted to further demonstrate in a mouse model that double combination therapies with exenatide, CsA and potassium canrenoate, after the onset of ischemia and prior to reperfusion, result in enhanced reduction of infarct size compared to respective monotherapies, and that triple combination therapy with exenatide, CsA and potassium canrenoate is more beneficial and advantageous compared to double combination therapies.

C57BL/6 mice were used in this study. Mice were males, 13-15 weeks in age. All animals were treated according to the Directive 2010/63/UE European Convention for the Protection of Vertebrate Animals used for Experimental and other Scientific Purposes, and conformed to the Guide for the Care and Use of Laboratory Animals published by the US National Institutes of Health (NIH Publication No. 85-23, revised 1985). Approvals from the Ethical Committees and the veterinary authorities were obtained before the study was started. Environmental controls in the animal rooms were set to maintain temperature of 22° to 28° C. and relative humidity between 30% and 70%. Room temperature and humidity were recorded hourly and monitored daily. There were approximately 10-15 air exchanges per hour in the animal rooms. Photoperiod was 12-hours light and 12-hours dark. Routine daily observations were performed. Standard laboratory mouse chow and filtered tap water was available ad libitum.

Exenatide (Byetta®; Eli Lilly Nederland B.V.], CsA (Sandimmun®, Novartis Pharma A.G., Switzerland) and potassium canrenoate (Sigma-Aldrich, Germany) are used as the test articles, either as monotherapies or in double or in triple combined therapy. Dosing solutions of exenatide, CsA and potassium canrenoate were prepared just before the administration to the mice. Normal saline (0.9% NaCl) was used as a control.

The test/control articles were given intravenously, under general anaesthesia, in order to mimic the expected route of administration in the clinical setting of acute myocardial infarction and primary percutaneous coronary intervention.

The study followed a predetermined placebo controlled design. In brief, 149 healthy, acclimatized, male mice were randomly assigned to one of twenty (20) study arms. In all groups, mice were subjected to 30 min regional ischemia of the heart (coronary occlusion), followed by 120 min (2 h) reperfusion. In all cases, treatments (intravenous bolus administration of saline or test articles or their combinations) were performed 20 min after the onset of ischemia (10 min before the initiation of reperfusion). The experiments were terminated 2 h post-reperfusion (end of study); irreversible myocardial injury (infarct size by histomorphometry) at this time-point was evaluated, and was the primary-end-point of the study. The study design is summarized in Table 11.

TABLE 11

Experimental protocol

| Study Group (no. of animals) | Ischemia Time | Reperfusion Time |
|---|---|---|
| CONTROL (n = 12) | 30 min (Last 10 min with saline) | 120 min of placebo (saline) |
| EXENATIDE 0.001 µg/Kg (n = 5) | 30 min (Last 10 min with exenatide) | 120 min of exenatide |
| EXENATIDE 0.005 µg/Kg (n = 8) | 30 min (Last 10 min with exenatide) | 120 min of exenatide |
| EXENATIDE 0.05 µg/Kg (n = 8) | 30 min (Last 10 min with exenatide) | 120 min of exenatide |
| EXENATIDE 0.15 µg/Kg (n = 7) | 30 min (Last 10 min with exenatide) | 120 min of exenatide |
| EXENATIDE 1.5 µg/Kg (n = 8) | 30 min (Last 10 min with exenatide) | 120 min of exenatide |
| CYCLOSPORINE 0.001 mg/Kg (n = 5) | 30 min (Last 10 min with cyclosporine) | 120 min of cyclosporine |
| CYCLOSPORINE 0.01 mg/Kg (n = 8) | 30 min (Last 10 min with cyclosporine) | 120 min of cyclosporine |
| CYCLOSPORINE 0.15 mg/Kg (n = 8) | 30 min (Last 10 min with cyclosporine) | 120 min of cyclosporine |
| CYCLOSPORINE 0.5 mg/Kg (n = 7) | 30 min (Last 10 min with cyclosporine) | 120 min of cyclosporine |
| CYCLOSPORINE 2.5 mg/Kg (n = 8) | 30 min (Last 10 min with cyclosporine) | 120 min of cyclosporine |
| P. CANRENOATE 0.03 mg/Kg (n = 8) | 30 min (Last 10 min with potassium canrenoate) | 120 min of potassium canrenoate |
| P. CANRENOATE 0.3 mg/Kg (n = 7) | 30 min (Last 10 min with potassium canrenoate) | 120 min of potassium canrenoate |
| P. CANRENOATE 1 mg/Kg (n = 8) | 30 min (Last 10 min with potassium canrenoate) | 120 min of potassium canrenoate |
| P. CANRENOATE 10 mg/Kg (n = 8) | 30 min (Last 10 min with potassium canrenoate) | 120 min of potassium canrenoate |
| EXENATIDE 0.05 µg/Kg + CYCLOSPORINE 0.15 mg/Kg (n = 5) | 30 min (Last 10 min with exenatide and cyclosporine) | 120 min of exenatide and cyclosporine |
| EXENATIDE 0.05 µg/Kg + P. CANRENOATE 1 mg/Kg (n = 11) | 30 min (Last 10 min with exenatide and potassium canrenoate) | 120 min of exenatide and potassium canrenoate |
| EXENATIDE 0.05 µg/Kg + P. CANRENOATE 10 mg/Kg (n = 6) | 30 min (Last 10 min with exenatide and potassium canrenoate) | 120 min of exenatide and potassium canrenoate |
| CYCLOSPORINE 0.15 mg/Kg + P. CANRENOATE 1 mg/Kg (n = 6) | 30 min (Last 10 min with cyclosporine and potassium canrenoate) | 120 min of cyclosporine and potassium canrenoate |
| EXENATIDE 0.05 µg/Kg + CYCLOSPORINE 0.15 mg/Kg + P. CANRENOATE 1 mg/Kg (n = 6) | 30 min (Last 10 min with exenatide and cyclosporine and potassium canrenoate) | 120 min of exenatide and cyclosporine and potassium canrenoate |

Anaesthesia/Surgical Preparation.

Mice were anaesthetized by intraperitoneal injection (0.01 ml/Kg) with a combination of ketamine, xylazine and atropine (final doses of ketamine, xylazine and atropine were 100, 20 and 0.6 mg/Kg, respectively). Anaesthetic depth was evaluated by loss of pedal reflex to toe-pinch stimulus and breathing rate. A tracheotomy was performed for artificial respiration at 120-150 breaths/min and positive end-expiratory pressure 2.0 (0.2 ml of total tidal volume; Flexivent rodent ventilator, Scireq, Montreal, ON, Canada). A thoracotomy was then performed between the fourth and fifth ribs and the pericardium carefully retracted to visualize the left anterior descending (LAD), which was ligated using an 8-0 prolene monofilament polypropylene suture placed 1 mm below the tip of the left auricle. The heart was allowed to stabilize for 12 min prior to ligation to induce ischemia. After the ischemic period, the ligature was released allowing reperfusion of myocardium. Throughout experiments, body temperature was maintained at 37±0.5° C. by way of a heating pad and monitored via a thermocouple inserted rectally.

Histopathology/Histomorphometry.

After reperfusion, animals were sacrificed with an intraperitoneal injection of the ketamine (200 mg/Kg) and xylazine (50 mg/Kg) anaesthetic mixture (0.02 ml/Kg) hearts were rapidly excited from mice and directly cannulated and washed with 2.5 ml of saline heparin 1% for blood removal. Five ml of 1% TTC phosphate buffer 37° C. were infused into the coronary circulation; the tissue was incubated for 5 min in the same buffer. Evans Blue 1% diluted in distilled water (2.5 ml) was the infused into the heart. Hearts were kept at −20° C. for 24 hours and then sliced in 1 mm sections parallel to the atrioventricular groove, and then fixed in 4% formalin overnight. Slices were then compressed between glass plates 1 mm apart and photographed with a Cannon Powershot A620 Digital Camera through a Zeiss 459300 microscope and measured with the Scion Image program. The areas of myocardial tissue at risk and infarcted were automatically transformed into volumes. Infarct and risk area volumes were expressed in $cm^3$. For each slide, the AAR was expressed as a percentage of the LV area (AAR/LV), and the IF was expressed as a percentage of the AAR (IF/AAR). In all cases, quantitative histomorphometry was performed by personnel blinded to the treatment assignment/study-design.

Data Analysis/Statistics.

All results are presented as mean+SEM. Comparisons of numeric variables among the groups were analyzed using an one-way analysis of variance (ANOVA) model with Bonferroni correction and with Tukey post hoc analysis. Analyses were performed using a Stata 13.1 statistical software package (StataCorp, TX, USA). A calculated P-value of less than 0.05 was considered to be statistically significant.

Animal Observations/Results.

The area of the left ventricle (LV) and the ischemic area (AAR) were similar in all animals and did not differ statistically between the study groups. The induction of ischemia (30 min) and reperfusion (120 min) in the control group resulted in significant injury to the myocardium of experimental animals (47.4±1.9%), indicating the sufficient implementation of the model and the reproducibility of the experimental procedure of the study.

The exenatide monotherapy (0.001 µg/kg-1.5 µg/Kg) caused a dose-response effect with the doses of 0.005 µg/kg and 0.05 µg/kg to cause a reduction of infarct size by 36.9% (29.9±1.8%; P<0.05) and 31.6% (32.4±1.9%; P<0.05), respectively, compared with the control group. The cyclosporine monotherapy (0.001 mg/kg-2.5 mg/Kg) caused a dose-response effect with the doses of 0.01 mg/kg and 0.15 mg/kg to cause a reduction of infarct size by 43.7% (26.7±2.8%; P<0.05) and 49.4% (24±1.9%; P<0.05), respectively, compared with the control group. The potassium canrenoate monotherapy (0.03 mg/kg-10 mg/Kg) caused a dose-response effect with the doses of 1 mg/kg and 10 mg/kg to cause a reduction of infarct size by 30% (33.2±2.4%; P<0.05) and 58.9% (19.5±2.5%; P<0.05), respectively, compared with the control group.

Double combination of exenatide and cyclosporine caused a reduction in the extent of infarct by 52.5% (22.5±2.3%; P<0.05) compared to the control group. However, this effect was not statistically significant compared to the respective monotherapy doses of exenatide and cyclosporine. The double combination of exenatide and potassium canrenoate caused a reduction in the extent of infarct by 70.9% (13.8±1.3%; P<0.01) compared to the control group. Interestingly, the effect of the combination was also statistically significant (P<0.05) compared to the respective doses of exenatide and potassium canrenoate monotherapies. However, when exenatide was combined with higher dose (10 mg/Kg) of potassium canrenoate reduced infarct size by 52.3% (22.6±2%), which was not statistically significant with the respective monotherapies. Double combination of cyclosporine and potassium canrenoate caused a reduction in the extent of infarct by 61.4% (18.3±2.6%; P<0.05) compared to the control group. However, this effect was not statistically significant compared to the respective monotherapy doses of cyclosporine and potassium canrenoate. Finally, a triple combination of exenatide, cyclosporine and potassium canrenoate caused a reduction in the extent of infarct by 56.7% (20.5±2%; P<0.05) compared to the control group. However, this effect was not statistically significant compared to the respective monotherapy doses of exenatide, cyclosporine and potassium canrenoate.

Table 12 presents data showing the ratios of area of risk to left ventricular and infarcted area to area of risk for each of group used in this study.

TABLE 12

Study histopathology results

| Group | AAR/LV (% mean ± SEM) | IF/AAR (% mean ± SEM) | Different (%) in IF/AAR from Control | Significance in IF/AAR versus Control | Significance in IF/AAR versus monotherapies |
|---|---|---|---|---|---|
| CONTROL (n = 12) | 53.1 ± 1.8 | 47.4 ± 1.9 | — | — | — |
| EXENATIDE 0.001 µg/Kg (n = 5) | 56.1 ± 2.5 | 44.8 ± 3.8 | −5.5 | ns | — |
| EXENATIDE 0.005 µg/Kg (n = 8) | 51.4 ± 4.5 | 29.9 ± 1.8 | −36.9 | P < 0.05 | — |
| EXENATIDE 0.05 µg/Kg (n = 8) | 53.1 ± 2.2 | 32.4 ± 1.9 | −31.6 | P < 0.05 | — |
| EXENATIDE 0.15 µg/Kg (n = 7) | 54.5 ± 2 | 41 ± 3 | −13.5 | ns | — |
| EXENATIDE 1.5 µg/Kg (n = 8) | 54.8 ± 2.6 | 45.4 ± 2.1 | −4.2 | ns | — |
| CYCLOSPORINE 0.001 mg/Kg (n = 5) | 58 ± 5.7 | 36.6 ± 2.4 | −22.8 | ns | — |
| CYCLOSPORINE 0.01 mg/Kg (n = 8) | 48.6 ± 2.82 | 26.7 ± 2.8 | −43.7 | P < 0.05 | — |
| CYCLOSPORINE 0.15 mg/Kg (n = 8) | 50.7 ± 2.9 | 24 ± 1.9 | −49.4 | P < 0.05 | — |
| CYCLOSPORINE 0.5 mg/Kg (n = 7) | 56.4 ± 3.6 | 33.6 ± 2.5 | −29.1 | P < 0.05 | — |

TABLE 12-continued

Study histopathology results

| Group | AAR/LV (% mean ± SEM) | IF/AAR (% mean ± SEM) | Different (%) in IF/AAR from Control | Significance in IF/AAR versus Control | Significance in IF/AAR versus monotherapies |
|---|---|---|---|---|---|
| CYCLOSPORINE 2.5 mg/Kg (n = 8) | 50.4 ± 1.9 | 30 ± 2.4 | −36.7 | P < 0.05 | — |
| P. CANRENOATE 0.03 mg/Kg (n = 8) | 59.4 ± 5.8 | 46 ± 2.5 | −3 | ns | — |
| P. CANRENOATE 0.3 mg/Kg (n = 7) | 55.5 ± 6.1 | 44 ± 3.2 | −7.2 | ns | — |
| P. CANRENOATE 1 mg/Kg (n = 8) | 52.4 ± 1.4 | 33.2 ± 2.4 | −30 | P < 0.05 | — |
| P. CANRENOATE 10 mg/Kg (n = 8) | 45.8 ± 1.2 | 19.5 ± 2.5 | −58.9 | P < 0.05 | — |
| EXENATIDE 0.05 µg/Kg + CYCLOSPORINE 0.15 mg/Kg (n = 5) | 54.8 ± 5.6 | 22.5 ± 2.3 | −52.5 | P < 0.05 | ns |
| EXENATIDE 0.05 µg/Kg + P. CANRENOATE 1 mg/Kg (n = 11) | 55.5 ± 2.9 | 13.8 ± 1.3 | −70.9 | P < 0.01 | P < 0.05 |
| EXENATIDE 0.05 µg/Kg + P. CANRENOATE 10 mg/Kg (n = 6) | 53.5 ± 3.1 | 22.6 ± 2 | −52.3 | P < 0.05 | ns |
| CYCLOSPORINE 0.15 mg/Kg + P. CANRENOATE 1 mg/Kg (n = 6) | 56.1 ± 4.4 | 18.3 ± 2.6 | −61.4 | P < 0.05 | ns |
| EXENATIDE 0.05 µg/Kg + CYCLOSPORINE 0.15 mg/Kg + P. CANRENOATE 1 mg/Kg (n = 6) | 55.7 ± 3.2 | 20.5 ± 2 | −56.7 | P < 0.05 | ns |

These results show that in an additional standardized animal (murine) model of acute myocardial ischemia and reperfusion injury, the combined therapy of exenatide, cyclosporine and potassium canrenoate when administrated as an IV bolus at 10 min before the initiation of reperfusion was able to produce a greater reduction in the myocardial infarct size compared to exenatide or CsA or potassium canrenoate monotherapy groups. It is of great interest that the present results provide strong evidence that the combination therapy of potassium canrenoate with exenatide reduced the extent of myocardial injury also in a synergistic manner, since the obtained combination reduction exceeds the sum of the respective monotherapies' reductions. Accordingly, these results demonstrate that in the therapy of myocardial reperfusion injury the combined administration of exenatide and potassium canrenoate provides the greatest cardioprotection effect compared to the respective monotherapies or other double or triple combinations. As such, combined exenatide, and potassium canrenoate is exceptionally useful in methods at preventing and treating ischemia-reperfusion injury in mammalian subjects.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

This invention includes all modifications and equivalents of the subject matter recited in the paragraphs appended hereto as permitted by applicable law.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

The citation and incorporation of patent documents herein is done for convenience only and does not reflect any view of the validity, patentability, and/or enforceability of such patent documents.

All headings and sub-headings are used herein for convenience only and should not be construed as limiting the invention in any way.

What is claimed is:

1. A method of treating ischemia or reperfusion injury, said method consisting of simultaneously or sequentially administering to a subject in need thereof a pharmaceutical composition consisting of exenatide or a pharmaceutically acceptable salt thereof, and a pharmaceutically acceptable carrier, diluent or excipient, and a pharmaceutical composition consisting of potassium canrenoate, and a pharmaceutically acceptable carrier, diluent or excipient, and wherein exenatide is administered at a dose in the range from about 0.05 to about 0.15 µg/kg and potassium canrenoate is administered at a dose in the range from about 1 to about 3 mg/kg, wherein the pharmaceutical compositions are administered parenterally.

2. The method according to claim 1, wherein the ischemia or reperfusion injury is ischemia or reperfusion injury of the brain, heart, lung, or kidney.

3. The method according to claim 1, wherein the pharmaceutical compositions are administered before reperfusion.

4. The method according to claim 1, wherein the pharmaceutical compositions are administered simultaneously to said subject.

5. The method according to claim 1, wherein the pharmaceutical compositions are administered sequentially.

6. The method according to claim 1, wherein the ischemia is myocardial ischemia.

7. The method according to claim 1, wherein the reperfusion injury is myocardial reperfusion injury or acute myocardial infarction.

8. The method according to claim 1, wherein the pharmaceutical compositions are administered intravenously.

9. The method according to claim 1, wherein the potassium canrenoate is administered at a dose of about 1 mg/kg.

10. The method according to claim 1, wherein the potassium canrenoate is administered at a dose of about 1 mg/kg, and the exenatide is administered at a dose of about 0.05 µg/kg.

11. A method of treating ischemia or reperfusion injury, said method consisting of administering to a subject in need thereof a pharmaceutical composition consisting of exenatide, or a pharmaceutically acceptable salt thereof, potassium canrenoate, and a pharmaceutically acceptable carrier, diluent or excipient, and wherein exenatide is administered at a dose in the range from about 0.05 to about 0.15 µg/kg and potassium canrenoate is administered at a dose in the range from about 1 to about 3 mg/kg, wherein the exenatide and potassium canrenoate are administered parenterally.

12. The method according to claim 11, wherein the potassium canrenoate is administered at a dose of about 1 mg/kg.

13. The method according to claim 11, wherein the potassium canrenoate is administered at a dose of about 1 mg/kg, and the exenatide is administered at a dose of about 0.05 µg/kg.

14. A method of treating ischemia or reperfusion injury, said method consisting of simultaneously or sequentially administering to a subject in need thereof exenatide, or a pharmaceutically acceptable salt thereof, and potassium canrenoate, and wherein exenatide is administered at a dose in the range from about 0.05 to about 0.15 µg/kg and potassium canrenoate is administered at a dose in the range from about 1 to about 3 mg/kg, wherein the exenatide and potassium canrenoate are administered parenterally.

15. The method according to claim 11 or 14, wherein the exenatide and potassium canrenoate are administered intravenously before reperfusion.

16. The method according to claim 11 or 14, wherein the ischemia is myocardial ischemia.

17. The method according to claim 11 or 14, wherein the reperfusion injury is myocardial reperfusion injury or acute myocardial infarction.

18. The method according to claim 14, wherein the exenatide and potassium canrenoate are administered simultaneously.

19. The method according to claim 14, wherein the exenatide and potassium canrenoate are administered sequentially.

20. The method according to claim 14, wherein the potassium canrenoate is administered at a dose of about 1 mg/kg.

21. The method according to claim 14, wherein the potassium canrenoate is administered at a dose of about 1 mg/kg, and the exenatide is administered at a dose of about 0.05 µg/kg.

* * * * *